United States Patent [19]

Smith et al.

[11] Patent Number: 5,408,038

[45] Date of Patent: Apr. 18, 1995

[54] NONNATURAL APOLIPOPROTEIN B-100 PEPTIDES AND APOLIPOPROTEIN B-100-APOLIPOPROTEIN A-I FUSION PEPTIDES

[75] Inventors: Richard S. Smith, Del Mar; Linda K. Curtiss, San Diego; Kanaka R. Koduri, San Diego; Joseph L. Witztum, San Diego; Stephen G. Young, Hillsborough, all of Calif.

[73] Assignee: The Scripps Research Institute, La Jolla, Calif.

[21] Appl. No.: 959,946

[22] Filed: Oct. 8, 1992

Related U.S. Application Data

[63] Continuation-in-part of Ser. No. 901,706, Jun. 18, 1992, abandoned, which is a continuation of Ser. No. 774,633, Oct. 9, 1991, abandoned.

[51] Int. Cl.⁶ .................... C07K 15/16; C07H 21/04; G01N 33/53
[52] U.S. Cl. ................................ 530/359; 536/23.5; 435/7.1
[58] Field of Search .................. 530/359; 536/23.5; 435/7.1

[56] References Cited

U.S. PATENT DOCUMENTS 4,745,055 5/1988 Schenk et al. .................. 435/7

OTHER PUBLICATIONS

Aisenberg, *Attorney's Dictionary of Patent Claims*, Matthew Bender, pp. A-2, A-3, B-28.1, B-29, B-30, L-22, L-23, O-16 (1993).

Noller, *Chemistry of Organic Compounds*, W. B. Saunders Company Philadelphia, p. 35 (1951).

Hopp/Wood, *Proc. Natl. Acad. Sci. USA*, 78:3824 (1981).

Hopp, T. P. Review article: Protein surface analysis, Methods for identifying antigenic determinants and other interaction sites. J. Immunol. Methods (1986) 8:1–18.

Karathanasis, S. K. et al. Isolation and characterization of the human apolipoprotein A-I gene, Proc. Natl. Acad. Sci. USA (1983) 80:6147–6151.

Cladaras, C. et al, The complete sequence and structural analysis of human apolipoprotein B-100: relationship between apoB-100 and apoB-48 forms. EMBO J. (1986) 5:3495–3507.

*Primary Examiner*—Margaret Parr
*Assistant Examiner*—David Schreiber
*Attorney, Agent, or Firm*—Welsh & Katz

[57] ABSTRACT

Methods and compositions are described for determining the level of low density lipoproteins (LDL) in plasma. Native apoprotein B-100 (apo B-100) present in LDL particles is immunologically mimicked by a polypeptide of the invention. A polypeptide includes an amino acid residue sequence corresponding to a pan epitope region of the target apoprotein. A preferred polypeptide is a fusion protein that simultaneously mimics native apo B-100 and native apo A-I. Improved assay systems and methods for determining HDL and LDL levels in a body fluid sample are also described.

12 Claims, 7 Drawing Sheets

GAGCTCCCCAGGACCTTTCAAATTCCTGGATACACTGTTCCAGTTGTCAATGTTGAAGTG
GluLeuProArgThrPheGlnIleProGlyTyrThrValProValValAsnValGluVal
aa 3214 (9642 bp)                                3233 (9699)

TCTCCATTCACCATAGAGATGTCGGCATTCGGCTATGTGTTCCCAAAGCAGTCAGCATG
SerProPheThrIleGluMetSerAlaPheGlyTyrValPheProLysAlaValSerMet
                                                 3253 (9759)

CCTAGTTTCTCCATCCTAGAGTTCTGACGTCCGTGTGCCTTCATACACATTAATCCTGCCA
ProSerPheSerIleLeuGlySerAspValArgValProSerTyrThrLeuIleLeuPro
                                                 3273 (9819)

TCATTAGAGCTGCCAGTCCCTTCATGCCCTAGAAATCTCAAGCTTTCTCTTCCAGATTTC
SerLeuGluLeuProValLeuHisValProArgAsnLeuLysLeuSerLeuProAspPhe
                                                 3293 (9879)

AAGGAATTGTGTACCATAAGCCCATATTTTTATTCCTGCCATGGGCAATATTACCTATGAT
LysGluLeuCysThrIleSerHisIlePheIleProAlaMetGlyAsnIleThrTyrAsp
                                                 3313 (9939)

TTCTCCTTTAAATCAAGTGTCATCACACTGAATACCAATGCTGAACTTTTTAACCAGTCA
PheSerPheLysSerValIleThrLeuAsnThrAsnAlaGluLeuPheAsnGlnSer
                                                 3333 (9999)

FIGURE 1A PRIOR ART

```
                                                           37-->
GATATTGTTGCTCATCTCCTTTCTTCATCTTCATCTGTCATTGATGCACTGCAGTACAAA
AspIleValAlaHisLeuLeuSerSerSerValIleAspAlaLeuGlnTyrLys
                                                    3353 (10,059)

TTAGAGGGCACCACAAGATTGACAAGAAAAAGGGGATTGAAGTTAGCCACAGCTCTGTCT
LeuGluGlyThrThrArgLeuThrArgLysArgGlyLeuLysLeuAlaThrAlaLeuSer
                                                    3373 (10,119)

34-->
CTGAGCAACAAATTTGTGGAGGTAGTCATAACAGTACTGTGAGCTTAACCACGAAAAAT
LeuSerAsnLysPheValGluGlySerHisAsnSerThrValSerLeuThrThrLysAsn
                                                    3393 (10,179)

ATGGAAGTGTCAGTGGCAACAACCACAAAAGCCCAATTCCAATTTTGAGAATGAATTC
MetGluValSerValAlaThrThrThrLysAlaGlnIleProIleLeuArgMetAsnPhe
                                                    3413 (10,239)

46-->
AAGCAAGAACTTAATGGAAATACCAAGTCAAAACCTACTGTCTCTTCCTCCCATGGAATTT
LysGlnGluLeuAsnGlyAsnThrLysSerLysProThrValSerSerMetGluPhe
                                                    3433 (10,299)

FIGURE 1B PRIOR ART
```

```
110-->
AAGTATGATTCAATTCTTCAATGCTGTACTCTACCGCTAAAGGAGCAGTTGACCACAAG
LysTyrAspPheAsnSerSerMetLeuTyrSerThrAlaLysGlyAlaValAspHisLys
                                                    3453 (10,359)

111-->
CTTAGCTTGGAAAGCCTCACCTCTTACTTTTCCATTGAGTCATCTACCAAAGGAGATGTC
LeuSerLeuGluSerLeuThrSerTyrPheSerIleGluSerSerThrLysGlyAspVal
                                                    3473 (10,419)

AAGGGTTCGGTTCTTTCTCGGGAATATATTCAGGAACTATTGCTAGTGAGGCCAACACTTAC
LysGlySerValLeuSerArgGluTyrSerGlyThrIleAlaSerGluAlaAsnThrTyr
                                                    3493 (10,479)

99<--
113-->
                 114-->
TTGAATTCCAAGAGCACACGGTCTTCAGTGAAGCTGCAGGGCACTTCCAAAATTGATGAT
LeuAsnSerLysSerThrArgSerSerValLysLeuGlnGlyThrSerLysIleAspAsp
                                                    3513 (10,539)

135<--
ATCTGGAACCTTGAAGTAAAAAGAAAATTTGCTGGAGAAGCCACACTCCAACGCATATAT
IleTrpAsnLeuGluValLysGluAsnPheAlaGlyGluAlaThrLeuGlnArgIleTyr
                                                    3533 (10,599)
```

FIGURE 1C PRIOR ART

```
134<---
TCCCTCTGGGAGCACAGTACGAAAAACCACTTACAGCTAGAGGGCCTCTTTTCACCAAC
SerLeuTrpGluHisSerThrLysAsnHisLeuGlnLeuGluGlyLeuPhePheThrAsn
                                       3553 (10,659)

133<---
GGAGAACATACAAGCAAAGCCACCCTGGAACTCTCTCCATGGCAAATGTCAGCTCTTGTT
GlyGluHisThrSerLysAlaThrLeuGluLeuLeuSerProTrpGlnMetSerAlaLeuVal
                                       3573 (10,719)

130<---
CAGGTCCATGCAAGTCAGCCCCAGTTCCTCCTTCCATGATTCCCTGACCTTGGC
GlnValHisAlaSerGlnProSerSerPheHisAspPheProAspLeuGly
                              3590 (10,770p)
```

FIGURE 1D PRIOR ART

```
ATG AAA GCT GCG GTG CTG ACC TTG GCC GTG CTC TTC CTG ACG GGG AGC      48
Met Lys Ala Ala Val Leu Thr Leu Ala Val Leu Phe Leu Thr Gly Ser
 1                    5                  10                  15

CAG GCT CGG CAT TTC TGG CAG CAA GAT GAA CCC CCC CAG AGC CCC TGG      96
Gln Ala Arg His Phe Trp Gln Gln Asp Glu Pro Pro Gln Ser Pro Trp
             20                  25                  30

GAT CGA GTG AAG GAC CTG TAC GTG GCC ACT GTG TAT GTG CTC AAA GAC     144
Asp Arg Val Lys Asp Leu Tyr Val Ala Thr Val Tyr Val Leu Lys Asp
         35                  40                  45

AGC GGC AGA GAC TAT GTG TCC CAG TTT GAA GGC TCC GCC TTG GGA AAA     192
Ser Gly Arg Asp Tyr Val Ser Gln Phe Glu Gly Ser Ala Leu Gly Lys
     50                  55                  60

CAG CTA AAC CTA AAG CTC CTT GAC AAC TGG GAC AGC GTG ACC TCC ACC     240
Gln Leu Asn Leu Lys Leu Leu Asp Asn Trp Asp Ser Val Thr Ser Thr
 65                  70                  75                  80

TTC AGC AAG CTG CGC GAA CAG CTC GGC CCT GTG ACC CAG GAG TTC TGG     288
Phe Ser Lys Leu Arg Glu Gln Leu Gly Pro Val Thr Gln Glu Phe Trp
             85                  90                  95
```

FIGURE 2A PRIOR ART

GAT AAC CTG GAA AAG GAG ACA GAG GGC CTG AGG CAG GAG ATG AGC AAG 336
Asp Asn Leu Glu Lys Glu Thr Glu Gly Leu Arg Gln Glu Met Ser Lys
        100                 105                 110

GAT CTG GAG GAG GTG AAG GCC AAG GTG CAG CCC TAC CTG GAC GAC TTC 384
Asp Leu Glu Glu Val Lys Ala Lys Val Gln Pro Tyr Leu Asp Asp Phe
        115                 120                 125

CAG AAG TGG CAG GAG GAG ATG GAG CTC TAC CGC CAG AAG GTG GAG 432
Gln Lys Trp Gln Glu Glu Met Glu Leu Tyr Arg Gln Lys Val Glu
    130                 135                 140

CCG CTG CGC GCA GAG CTC CAA GAG GGC GCC CGC CAG AAG CTG CAC GAG 480
Pro Leu Arg Ala Glu Leu Gln Glu Gly Ala Arg Gln Lys Leu His Glu
145                 150                 155                 160

CTG CAA GAG AAG CTG AGC CCA CTG GGC GAG GAG ATG CGC GAC CGC GCG 528
Leu Gln Glu Lys Leu Ser Pro Leu Gly Glu Glu Met Arg Asp Arg Ala
        165                 170                 175

CGC GCC CAT GTG GAC GCG CTG CGC ACG CAT CTG GCC CCC TAC AGC GAC 576
Arg Ala His Val Asp Ala Leu Arg Thr His Leu Ala Pro Tyr Ser Asp
    180                 185                 190

FIGURE 2B PRIOR ART

GAG CTG CGC CAG CGC TTG GCC GCG CGC CTT GAG GCT CTC AAG GAG AAC 624
Glu Leu Arg Gln Arg Leu Ala Ala Arg Leu Glu Ala Leu Lys Glu Asn
         195                 200                 205

GGC GGC GCC AGA CTG GCC GAG TAC CAC GCC AAG GCC ACC GAG CAT CTG 672
Gly Gly Ala Arg Leu Ala Glu Tyr His Ala Lys Ala Thr Glu His Leu
         210                 215                 220

AGC ACG CTC AGC GAG AAG CCC GCG CTC GAG GAC CTC CGC CAA 720
Ser Thr Leu Ser Glu Lys Pro Ala Leu Glu Asp Leu Arg Gln
         225                 230                 235                 240

GGC CTG CTG CCC GTG CTG GAG AGC TTC AAG GTC AGC TTC CTG AGC GCT 768
Gly Leu Leu Pro Val Leu Glu Ser Phe Lys Val Ser Phe Leu Ser Ala
         245                 250                 255

CTC GAG GAG TAC ACT AAG AAG CTC AAC ACC CAG 801
Leu Glu Glu Tyr Thr Lys Lys Leu Asn Thr Gln
         260                 265

FIGURE 2C PRIOR ART

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
( A ) LENGTH: 377 amino acids
( B ) TYPE: amino acid
( D ) TOPOLOGY: linear ( i i ) MOLECULE TYPE: protein ( x i ) SEQUENCE DESCRIPTION: SEQ ID NO:1:

| Glu | Leu | Pro | Arg | Thr | Phe | Gln | Ile | Pro | Gly | Tyr | Thr | Val | Pro | Val | Val |
|---|---|---|---|---|---|---|---|---|---|---|---|---|---|---|---|
| 1 | | | | 5 | | | | | 10 | | | | | 15 | |

Asn Val Glu Val Ser Pro Phe Thr Ile Glu Met Ser Ala Phe Gly Tyr
          20                  25                  30

Val Phe Pro Lys Ala Val Ser Met Pro Ser Phe Ser Ile Leu Gly Ser
          35                  40                  45

Asp Val Arg Val Pro Ser Tyr Thr Leu Ile Leu Pro Ser Leu Glu Leu
          50                  55                  60

Pro Val Leu His Val Pro Arg Asn Leu Lys Leu Ser Leu Pro Asp Phe
65                   70                  75                  80

Lys Glu Leu Cys Thr Ile Ser His Ile Phe Ile Pro Ala Met Gly Asn
                85                  90                  95

Ile Thr Tyr Asp Phe Ser Phe Lys Ser Ser Val Ile Thr Leu Asn Thr
            100                 105                 110

Asn Ala Glu Leu Phe Asn Gln Ser Asp Ile Val Ala His Leu Leu Ser
            115                 120                 125

Ser Ser Ser Ser Val Ile Asp Ala Leu Gln Tyr Lys Leu Glu Gly Thr
    130                 135                 140

Thr Arg Leu Thr Arg Lys Arg Gly Leu Lys Leu Ala Thr Ala Leu Ser
145                 150                 155                 160

Leu Ser Asn Lys Phe Val Glu Gly Ser His Asn Ser Thr Val Ser Leu
                165                 170                 175

Thr Thr Lys Asn Met Glu Val Ser Val Ala Thr Thr Lys Ala Gln
            180                 185                 190

Ile Pro Ile Leu Arg Met Asn Phe Lys Gln Glu Leu Asn Gly Asn Thr
        195                 200                 205

Lys Ser Lys Pro Thr Val Ser Ser Met Glu Phe Lys Tyr Asp Phe
210                 215                 220

Asn Ser Ser Met Leu Tyr Ser Thr Ala Lys Gly Ala Val Asp His Lys
225                 230                 235                 240

Leu Ser Leu Glu Ser Leu Thr Ser Tyr Phe Ser Ile Glu Ser Ser Thr
                245                 250                 255

Lys Gly Asp Val Lys Gly Ser Val Leu Ser Arg Glu Tyr Ser Gly Thr
            260                 265                 270

Ile Ala Ser Glu Ala Asn Thr Tyr Leu Asn Ser Lys Ser Thr Arg Ser
        275                 280                 285

Ser Val Lys Leu Gln Gly Thr Ser Lys Ile Asp Asp Ile Trp Asn Leu
    290                 295                 300

Glu Val Lys Glu Asn Phe Ala Gly Glu Ala Thr Leu Gln Arg Ile Tyr
305                 310                 315                 320

Ser Leu Trp Glu His Ser Thr Lys Asn His Leu Gln Leu Glu Gly Leu
                325                 330                 335

Phe Phe Thr Asn Gly Glu His Thr Ser Lys Ala Thr Leu Glu Leu Ser
            340                 345                 350

Pro Trp Gln Met Ser Ala Leu Val Gln Val His Ala Ser Gln Pro Ser
        355                 360                 365

Ser Phe His Asp Phe Pro Asp Leu Gly
    370                 375

( 2 ) INFORMATION FOR SEQ ID NO:2:

( i ) SEQUENCE CHARACTERISTICS:
        ( A ) LENGTH: 1131 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:

( A ) NAME/KEY: CDS
( B ) LOCATION: 1..1131

( x i ) SEQUENCE DESCRIPTION: SEQ ID NO:2:

| | | | | | | | | | | | | | | | | |
|---|---|---|---|---|---|---|---|---|---|---|---|---|---|---|---|---|
| GAG | CTC | CCC | AGG | ACC | TTT | CAA | ATT | CCT | GGA | TAC | ACT | GTT | CCA | GTT | GTC | 48 |
| Glu | Leu | Pro | Arg | Thr | Phe | Gln | Ile | Pro | Gly | Tyr | Thr | Val | Pro | Val | Val | |
| 1 | | | | 5 | | | | | 10 | | | | | 15 | | |
| AAT | GTT | GAA | GTG | TCT | CCA | TTC | ACC | ATA | GAG | ATG | TCG | GCA | TTC | GGC | TAT | 96 |
| Asn | Val | Glu | Val | Ser | Pro | Phe | Thr | Ile | Glu | Met | Ser | Ala | Phe | Gly | Tyr | |
| | | | 20 | | | | | 25 | | | | | 30 | | | |
| GTG | TTC | CCA | AAA | GCA | GTC | AGC | ATG | CCT | AGT | TTC | TCC | ATC | CTA | GGT | TCT | 144 |
| Val | Phe | Pro | Lys | Ala | Val | Ser | Met | Pro | Ser | Phe | Ser | Ile | Leu | Gly | Ser | |
| | | 35 | | | | | 40 | | | | | 45 | | | | |
| GAC | GTC | CGT | GTG | CCT | TCA | TAC | ACA | TTA | ATC | CTG | CCA | TCA | TTA | GAG | CTG | 192 |
| Asp | Val | Arg | Val | Pro | Ser | Tyr | Thr | Leu | Ile | Leu | Pro | Ser | Leu | Glu | Leu | |
| | 50 | | | | | 55 | | | | | 60 | | | | | |
| CCA | GTC | CTT | CAT | GTC | CCT | AGA | AAT | CTC | AAG | CTT | TCT | CTT | CCA | GAT | TTC | 240 |
| Pro | Val | Leu | His | Val | Pro | Arg | Asn | Leu | Lys | Leu | Ser | Leu | Pro | Asp | Phe | |
| 65 | | | | | 70 | | | | | 75 | | | | | 80 | |
| AAG | GAA | TTG | TGT | ACC | ATA | AGC | CAT | ATT | TTT | ATT | CCT | GCC | ATG | GGC | AAT | 288 |
| Lys | Glu | Leu | Cys | Thr | Ile | Ser | His | Ile | Phe | Ile | Pro | Ala | Met | Gly | Asn | |
| | | | | 85 | | | | | 90 | | | | | 95 | | |
| ATT | ACC | TAT | GAT | TTC | TCC | TTT | AAA | TCA | AGT | GTC | ATC | ACA | CTG | AAT | ACC | 336 |
| Ile | Thr | Tyr | Asp | Phe | Ser | Phe | Lys | Ser | Ser | Val | Ile | Thr | Leu | Asn | Thr | |
| | | | 100 | | | | | 105 | | | | | 110 | | | |
| AAT | GCT | GAA | CTT | TTT | AAC | CAG | TCA | GAT | ATT | GTT | GCT | CAT | CTC | CTT | TCT | 384 |
| Asn | Ala | Glu | Leu | Phe | Asn | Gln | Ser | Asp | Ile | Val | Ala | His | Leu | Leu | Ser | |
| | | 115 | | | | | 120 | | | | | 125 | | | | |
| TCA | TCT | TCA | TCT | GTC | ATT | GAT | GCA | CTG | CAG | TAC | AAA | TTA | GAG | GGC | ACC | 432 |
| Ser | Ser | Ser | Ser | Val | Ile | Asp | Ala | Leu | Gln | Tyr | Lys | Leu | Glu | Gly | Thr | |
| | 130 | | | | | 135 | | | | | 140 | | | | | |
| ACA | AGA | TTG | ACA | AGA | AAA | AGG | GGA | TTG | AAG | TTA | GCC | ACA | GCT | CTG | TCT | 480 |
| Thr | Arg | Leu | Thr | Arg | Lys | Arg | Gly | Leu | Lys | Leu | Ala | Thr | Ala | Leu | Ser | |
| 145 | | | | | 150 | | | | | 155 | | | | | 160 | |
| CTG | AGC | AAC | AAA | TTT | GTG | GAG | GGT | AGT | CAT | AAC | AGT | ACT | GTG | AGC | TTA | 528 |
| Leu | Ser | Asn | Lys | Phe | Val | Glu | Gly | Ser | His | Asn | Ser | Thr | Val | Ser | Leu | |
| | | | | 165 | | | | | 170 | | | | | 175 | | |
| ACC | ACG | AAA | AAT | ATG | GAA | GTG | TCA | GTG | GCA | ACA | ACC | ACA | AAA | GCC | CAA | 576 |
| Thr | Thr | Lys | Asn | Met | Glu | Val | Ser | Val | Ala | Thr | Thr | Thr | Lys | Ala | Gln | |
| | | | 180 | | | | | 185 | | | | | 190 | | | |
| ATT | CCA | ATT | TTG | AGA | ATG | AAT | TTC | AAG | CAA | GAA | CTT | AAT | GGA | AAT | ACC | 624 |
| Ile | Pro | Ile | Leu | Arg | Met | Asn | Phe | Lys | Gln | Glu | Leu | Asn | Gly | Asn | Thr | |
| | | 195 | | | | | 200 | | | | | 205 | | | | |
| AAG | TCA | AAA | CCT | ACT | GTC | TCT | TCC | TCC | ATG | GAA | TTT | AAG | TAT | GAT | TTC | 672 |
| Lys | Ser | Lys | Pro | Thr | Val | Ser | Ser | Ser | Met | Glu | Phe | Lys | Tyr | Asp | Phe | |
| | 210 | | | | | 215 | | | | | 220 | | | | | |
| AAT | TCT | TCA | ATG | CTG | TAC | TCT | ACC | GCT | AAA | GGA | GCA | GTT | GAC | CAC | AAG | 720 |
| Asn | Ser | Ser | Met | Leu | Tyr | Ser | Thr | Ala | Lys | Gly | Ala | Val | Asp | His | Lys | |
| 225 | | | | | 230 | | | | | 235 | | | | | 240 | |
| CTT | AGC | TTG | GAA | AGC | CTC | ACC | TCT | TAC | TTT | TCC | ATT | GAG | TCA | TCT | ACC | 768 |
| Leu | Ser | Leu | Glu | Ser | Leu | Thr | Ser | Tyr | Phe | Ser | Ile | Glu | Ser | Ser | Thr | |
| | | | | 245 | | | | | 250 | | | | | 255 | | |
| AAA | GGA | GAT | GTC | AAG | GGT | TCG | GTT | CTT | TCT | CGG | GAA | TAT | TCA | GGA | ACT | 816 |
| Lys | Gly | Asp | Val | Lys | Gly | Ser | Val | Leu | Ser | Arg | Glu | Tyr | Ser | Gly | Thr | |
| | | | 260 | | | | | 265 | | | | | 270 | | | |
| ATT | GCT | AGT | GAG | GCC | AAC | ACT | TAC | TTG | AAT | TCC | AAG | AGC | ACA | CGG | TCT | 864 |
| Ile | Ala | Ser | Glu | Ala | Asn | Thr | Tyr | Leu | Asn | Ser | Lys | Ser | Thr | Arg | Ser | |
| | | 275 | | | | | 280 | | | | | 285 | | | | |
| TCA | GTG | AAG | CTG | CAG | GGC | ACT | TCC | AAA | ATT | GAT | GAT | ATC | TGG | AAC | CTT | 912 |
| Ser | Val | Lys | Leu | Gln | Gly | Thr | Ser | Lys | Ile | Asp | Asp | Ile | Trp | Asn | Leu | |
| | 290 | | | | | 295 | | | | | 300 | | | | | |
| GAA | GTA | AAA | GAA | AAT | TTT | GCT | GGA | GAA | GCC | ACA | CTC | CAA | CGC | ATA | TAT | 960 |

|   |   |   |   |   |   |   |   |   |   |   |   |   |   |   |   |
|---|---|---|---|---|---|---|---|---|---|---|---|---|---|---|---|
| Glu | Val | Lys | Glu | Asn | Phe | Ala | Gly | Glu | Ala | Thr | Leu | Gln | Arg | Ile | Tyr |
| 305 |     |     |     | 310 |     |     |     |     | 315 |     |     |     |     |     | 320 |

```
TCC CTC TGG GAG CAC AGT ACG AAA AAC CAC TTA CAG CTA GAG GGC CTC       1008
Ser Leu Trp Glu His Ser Thr Lys Asn His Leu Gln Leu Glu Gly Leu
                325                 330                 335

TTT TTC ACC AAC GGA GAA CAT ACA AGC AAA GCC ACC CTG GAA CTC TCT       1056
Phe Phe Thr Asn Gly Glu His Thr Ser Lys Ala Thr Leu Glu Leu Ser
            340                 345                 350

CCA TGG CAA ATG TCA GCT CTT GTT CAG GTC CAT GCA AGT CAG CCC AGT       1104
Pro Trp Gln Met Ser Ala Leu Val Gln Val His Ala Ser Gln Pro Ser
        355                 360                 365

TCC TTC CAT GAT TTC CCT GAC CTT GGC                                   1131
Ser Phe His Asp Phe Pro Asp Leu Gly
370                 375
```

( 2 ) INFORMATION FOR SEQ ID NO:3:

( i ) SEQUENCE CHARACTERISTICS:
        ( A ) LENGTH: 267 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln
            260                 265
```

( 2 ) INFORMATION FOR SEQ ID NO:4:

( i ) SEQUENCE CHARACTERISTICS:
        ( A ) LENGTH: 801 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..801

( x i ) SEQUENCE DESCRIPTION: SEQ ID NO:4:

```
ATG AAA GCT GCG GTG CTG ACC TTG GCC GTG CTC TTC CTG ACG GGG AGC      48
Met Lys Ala Ala Val Leu Thr Leu Ala Val Leu Phe Leu Thr Gly Ser
 1               5                  10                  15

CAG GCT CGG CAT TTC TGG CAG CAA GAT GAA CCC CCC CAG AGC CCC TGG      96
Gln Ala Arg His Phe Trp Gln Gln Asp Glu Pro Pro Gln Ser Pro Trp
             20                  25                  30

GAT CGA GTG AAG GAC CTG GCC ACT GTG TAC GTG GAT GTG CTC AAA GAC     144
Asp Arg Val Lys Asp Leu Ala Thr Val Tyr Val Asp Val Leu Lys Asp
         35                  40                  45

AGC GGC AGA GAC TAT GTG TCC CAG TTT GAA GGC TCC GCC TTG GGA AAA     192
Ser Gly Arg Asp Tyr Val Ser Gln Phe Glu Gly Ser Ala Leu Gly Lys
     50                  55                  60

CAG CTA AAC CTA AAG CTC CTT GAC AAC TGG GAC AGC GTG ACC TCC ACC     240
Gln Leu Asn Leu Lys Leu Leu Asp Asn Trp Asp Ser Val Thr Ser Thr
 65                  70                  75                  80

TTC AGC AAG CTG CGC GAA CAG CTC GGC CCT GTG ACC CAG GAG TTC TGG     288
Phe Ser Lys Leu Arg Glu Gln Leu Gly Pro Val Thr Gln Glu Phe Trp
                 85                  90                  95

GAT AAC CTG GAA AAG GAG ACA GAG GGC CTG AGG CAG GAG ATG AGC AAG     336
Asp Asn Leu Glu Lys Glu Thr Glu Gly Leu Arg Gln Glu Met Ser Lys
            100                 105                 110

GAT CTG GAG GAG GTG AAG GCC AAG GTG CAG CCC TAC CTG GAC GAC TTC     384
Asp Leu Glu Glu Val Lys Ala Lys Val Gln Pro Tyr Leu Asp Asp Phe
        115                 120                 125

CAG AAG AAG TGG CAG GAG GAG ATG GAG CTC TAC CGC CAG AAG GTG GAG     432
Gln Lys Lys Trp Gln Glu Glu Met Glu Leu Tyr Arg Gln Lys Val Glu
    130                 135                 140

CCG CTG CGC GCA GAG CTC CAA GAG GGC GCG CGC CAG AAG CTG CAC GAG     480
Pro Leu Arg Ala Glu Leu Gln Glu Gly Ala Arg Gln Lys Leu His Glu
145                 150                 155                 160

CTG CAA GAG AAG CTG AGC CCA CTG GGC GAG GAG ATG CGC GAC CGC GCG     528
Leu Gln Glu Lys Leu Ser Pro Leu Gly Glu Glu Met Arg Asp Arg Ala
                165                 170                 175

CGC GCC CAT GTG GAC GCG CTG CGC ACG CAT CTG GCC CCC TAC AGC GAC     576
Arg Ala His Val Asp Ala Leu Arg Thr His Leu Ala Pro Tyr Ser Asp
            180                 185                 190

GAG CTG CGC CAG CGC TTG GCC GCG CGC CTT GAG GCT CTC AAG GAG AAC     624
Glu Leu Arg Gln Arg Leu Ala Ala Arg Leu Glu Ala Leu Lys Glu Asn
        195                 200                 205

GGC GGC GCC AGA CTG GCC GAG TAC CAC GCC AAG GCC ACC GAG CAT CTG     672
Gly Gly Ala Arg Leu Ala Glu Tyr His Ala Lys Ala Thr Glu His Leu
    210                 215                 220

AGC ACG CTC AGC GAG AAG GCC AAG CCC GCG CTC GAG GAC CTC CGC CAA     720
Ser Thr Leu Ser Glu Lys Ala Lys Pro Ala Leu Glu Asp Leu Arg Gln
225                 230                 235                 240

GGC CTG CTG CCC GTG CTG GAG AGC TTC AAG GTC AGC TTC CTG AGC GCT     768
Gly Leu Leu Pro Val Leu Glu Ser Phe Lys Val Ser Phe Leu Ser Ala
                245                 250                 255

CTC GAG GAG TAC ACT AAG AAG CTC AAC ACC CAG                         801
```

Leu Glu Glu Tyr Thr Lys Lys Leu Asn Thr Gln
         260                 265

( 2 ) INFORMATION FOR SEQ ID NO:5:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

Lys Val Gln Pro Tyr Leu Asp Asp Phe Gln Lys Lys Trp Gln Glu Glu
 1           5                  10                 15

( 2 ) INFORMATION FOR SEQ ID NO:6:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

Gly Gly Gly Gly Ser
 1           5

( 2 ) INFORMATION FOR SEQ ID NO:7:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

ATGCGGATCC AAATTAGAGG GCACCACAAG A                          3 1

( 2 ) INFORMATION FOR SEQ ID NO:8:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

ATGCGGATCC ACTGTGAGCT TAACCACGAA A                          3 1

( 2 ) INFORMATION FOR SEQ ID NO:9:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

ATGCGGATCC AATGAATACC AAGTCAAAA                            2 9

( 2 ) INFORMATION FOR SEQ ID NO:10:

( i ) SEQUENCE CHARACTERISTICS:

( A ) LENGTH: 34 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:10:

ATGCGGATCC TCCTCCATGG AATTTAAGTA TGAT   34

( 2 ) INFORMATION FOR SEQ ID NO:11:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:11:

ATGCCTCGAG TCCTCCATGG AATTTAAGTA TGAT   34

( 2 ) INFORMATION FOR SEQ ID NO:12:

( i ) SEQUENCE CHARACTERISTICS:
( A ) LENGTH: 43 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:12:

ATAGCTGCAG TTTGGAAGTG CCCTGGAGCT TCACTGAAGA CCG   43

( 2 ) INFORMATION FOR SEQ ID NO:13:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:13:

TTAACTGCAG CTATTAGCCA AGGTCAGGGA AATCATG   37

( 2 ) INFORMATION FOR SEQ ID NO:14:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:14:

AATTCTGCAG TTATCAGCCG GGAGAGAGTT CCAGGGT   37

( 2 ) INFORMATION FOR SEQ ID NO:15:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( i i ) MOLECULE TYPE: DNA (genomic)

(xi) SEQUENCE DESCRIPTION: SEQ ID NO:15:

AATTCTGCAG TTATCAGTGT AAGTGGTTTT TCGTACT 37

(2) INFORMATION FOR SEQ ID NO:16:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

AATTCTGCAG TTATCAAAAA TTTTCTTTTA CTTCAAG 37

(2) INFORMATION FOR SEQ ID NO:17:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

ATGCGGATCC AAATTAGAGG GCACCACAAG A 31

(2) INFORMATION FOR SEQ ID NO:18:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

GTGCCCTGCA GTTATCACTT CACTGAAGAC CGTGTGCT 38

(2) INFORMATION FOR SEQ ID NO:19:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

ATGTCTGCAG CGGCATTTCT GGCAGCAA 28

(2) INFORMATION FOR SEQ ID NO:20:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

GTGCCCTGCA GTTATCATTG GCGGAGGTCC TCGAGCGC 38

NONNATURAL APOLIPOPROTEIN B-100 PEPTIDES AND APOLIPOPROTEIN B-100-APOLIPOPROTEIN A-I FUSION PEPTIDES

This invention was made with government support under Contract No. HL 14197 awarded by the National Institutes of Health. The government has certain rights in the invention.

CROSS-REFERENCE TO RELATED APPLICATIONS

This is a continuation-in-part of application Ser. No. 07/901,706, filed Jun. 18, 1992, now abandoned that was a continuation of application Ser. No. 07/774,633, filed Oct. 9, 1991, now abandoned.

TECHNICAL FIELD

The present invention relates to assays of lipoprotein markers for abnormal lipid metabolism. The invention particularly relates to assays of human plasma for lipoproteins containing apoproteins B-100 and A-I, and the use of a polypeptide that contains a pan epitope of at least the apo B-100 protein along with antibodies that immunoreact with at least that epitope.

BACKGROUND

Lipoproteins are the primary carriers of plasma cholesterol, triacylglycerols, and other lipids. The lipoproteins are micellar lipid-protein complexes consisting of a hydrophobic lipid core surrounded by a shell of polar lipids and apoproteins. Lipoproteins are characterized by their buoyant densities which have resulted in identification of at least six major density classes: chylomicrons, very low-density lipoproteins (VLDL), intermediate-density lipoproteins (IDL), low-density lipoproteins (LDL), lipoprotein(a)s (Lp(a)), and high-density lipoproteins (HDL). At least ten apoproteins associated with these lipoproteins have been isolated and characterized: A-1, A-2, A-4, B-48, B-100, C-1, C-2, C-3, E, and apo(a). All of these apoproteins, except B-48 and B-100, are water-soluble and exchange readily between lipoproteins of different classes.

Many studies have now established an inverse relationship between plasma HDL cholesterol levels and risk of coronary artery disease (CAD), i.e., elevated levels of plasma cholesterol found in HDL particles correlate with a reduced risk of CAD. See, e.g., Goldbourt et al., Int. J. Epidemiol., 15:51–55 (1986). Similarly, many studies have shown that plasma levels of apoprotein A-I (apo A-I), the major protein component of HDL, are also inversely related to the risk of CAD.

Because of the inverse correlation of HDL levels with CAD, extensive research has been directed towards determining the role of HDL in lipid metabolism. Functionally, HDL is now believed to mediate the removal of cholesterol released into the plasma from dying cells and from membranes undergoing turnover. It is believed that an acyl transferase in HDL esterifies these cholesterol molecules, which are then rapidly shuttled to VLDL or LDL particles by a transfer protein. See, generally, Stryer L., Biochemistry, 3rd ed., W. H. Freeman and Co., New York, (1988), pp 560–564.

The amino acid residue sequence of human apo A-I has been determined by Edman degradation of the protein [Brewer et al., Biochem. Biophys. Res. Comm., 80:623–630 (1978)] and by sequencing full-length apo A-I cDNA [Seilhamer et al., DNA, 3(4):309 (1984)]. These studies report that mature apo A-I is a single chain protein of 243 amino acid residues.

The conformation of the A-I protein in HDL particles is not known [Curtiss et al., J. Biol. Chem., 263:13779 (1988)]. Additionally, immunochemical characterization of native apo A-I, i.e., apo A-I as it is found on HDL particles, has been problematic because of its antigenic heterogeneity and instability. The antigenic heterogeneity of native apo A-I appears to be due to masking of some epitopes by lipids in the intact HDL particle or due to a dependency of the antibody-binding ability of some epitopes upon conformations of native apo A-I in the presence of lipids or other HDL-associated proteins, e.g., the A-2 protein. The antigenic instability of native apo A-I, as manifested by its changing immunoreactivity over time with defined antisera, appears to be due to such phenomena as self-association and deamidation, both of which have been shown to occur in vitro. See Curtiss et al. in "Proceeding of the Workshop on Lipoprotein Heterogeneity", ed. by Lippel, National Institutes of Health Publication No. 87-2646, pp. 363–377 (1987). Further, the effects of storage and NaOH treatment on native apo A-I immunoreactivity are similar, although not identical, which suggests that other processes may be involved in the loss of immunoreactivity during storage than deamidation alone [Milthorp et al., Arterio., 6:285–296 (1986)].

The antigenic heterogeneity and instability of native apo A-I have made it difficult to develop immunoassays for native apo A-I in patient vascular fluid samples. This is due, at least in part, to proposed methods requiring the use of a reference material (standard) that has an immunoreactivity with anti-apo A-I antibodies comparable to the immunoreactivity of native apo A-I with the anti-apo A-I antibodies.

Recently, efforts to overcome the problems associated with the antigenic heterogeneity and instability of native apo A-I have focused on using monoclonal antibodies (Mabs) to identify epitopes on native apo A-I molecules, which expression is consistent or "conserved" under specific isolation and storage conditions. Such epitopes are referred to as "conserved native epitopes".

Conserved native apo A-I epitopes are reported to be defined by the 1–15 and 90–105 amino acid sequences of apo A-I [Curtiss et al., J. Biol. Chem., 263:13779 (1988)]. Synthetic polypeptides representing residues 1–15 and 90–105 are reported to inhibit HDL-binding of monoclonal antibodies AI-16 and AI-18, respectively. The synthetic polypeptide representing apo A-I residue sequence 90–105 and the AI-18 monoclonal antibodies are the subjects of U.S. Pat. No. 5,055,396. Other monoclonal antibodies include Mabs AI-4, AI-7, AI-9, and AI-11, which are reported in U.S. Pat. No. 4,677,057 to be immunoreactive with native apo A-I; however, the regions of apo A-I that define the epitopes bound by these antibodies have not been reported. The disclosures of U.S. Pat. No. 5,055,396 and U.S. Pat. No. 4,677,057 are incorporated herein by reference.

Additionally, certain monoclonal antibodies are reported to act as anti-apo A-I "pan" antibodies, i.e., antibodies that bind most, if not all, species of native apo A-I in plasma [Hogle et al., J. Lipid. Res., 29:1221–1229 (1988); Curtiss et al., in "Biotechnology of Dyslipoproteinemias: Clinical Applications in Diagnosis and Control" Lenfant et al., eds, pp. 217–226, Raven Press (New York), 1989]. Exemplary monoclonal antibodies in this regard include AI-10, AI-11, AI-12, AI-13, and AI-14, as discussed in U.S. Pat. No. 5,126,240 which disclosures are incorporated herein by reference. The epitopes on native apo A-I molecules with which these antibodies immunoreact have not been identified.

An antibody composition that immunoreacts with about 90 percent or more of native apo A-2 is referred to herein as a pan antibody composition, or pan antibodies. That composition can contain polyclonal antibodies, but more preferably contains one or more monoclonal antibodies as are described in the before-cited patents and patent applications. The single epitope or plurality of epitopes bound by pan antibodies is referred to herein as a pan epitope.

Contrary to the relationship of HDL levels to CAD, high levels of serum LDL have been correlated with abnormal lipid metabolism and CAD [Brown et al., New Engl. J. of Med., 323(19):1289 (1990). During normal lipid metabolism, LDL particles transport cholesterol to peripheral tissues and regulate de novo cholesterol synthesis at these sites. The particles bind to extracellular LDL receptors at these sites and are taken into the cells by endocytosis [Anderson et al., Cell, 10:351 (1977)]. The particles are chemically broken down within the cell, releasing cholesterol and amino acids. The released cholesterol molecules control feedback mechanisms that regulate de novo cholesterol synthesis and control synthesis of cholesterol receptors by the cells. See, generally, Stryer L., supra.

The basis for the relationship between LDL and CAD is believed to be due primarily to deposition of cholesterol on the arterial intima, in the form of atheromatous plaques, when high concentrations of LDL-cholesterol occur in the plasma. High plasma levels of LDL can occur when the diet is enriched in cholesterol or when certain genetic disorders, such as familial hypercholesterolemia (FH), are present. The molecular defect in most cases of FH is an absence or deficiency of functional LDL receptors. Homozygotes of FH typically have severely elevated cholesterol levels (680 mg/dl) and usually die of CAD in childhood. Heterozygotes (1 in 500 persons) typically show elevated cholesterol levels (300 mg/dl) and have increased CAD risk.

Structurally, LDL particles have a cholesterol core comprising about 1500 esterified cholesterol molecules surrounded by a shell of phospholipids, unesterified cholesterol molecules, and a single molecule of apoprotein B-100 (apo B-100). The hydrophilic shell of an LDL particle facilitates hydration and suspension of the particle in plasma. Cellular LDL receptors recognize and bind to native apo B-100, i.e., as it appears in LDL particles, thereby extracting LDL particles from the plasma. Hence, the B-100 protein is critical for effective receptor-mediated uptake and clearance of LDL particles from circulation. Accordingly, investigators have suggested that plasma levels of native apo B-100 actually may be more predictive of CAD risk than plasma LDL cholesterol levels [Sniderman et al., Proc. Natl. Acad. Sci. U.S.A., 77:604–608 (1980); Sniderman et al., Arteriosclerosis, 10(5):665 (1990); Albers et al., Clinics in Laboratory Medicine, 9(1):137 (1989)].

The B-100 protein is also found in VLDL and IDL particles, which are comprised of endogenous triacylglycerol and cholesterol ester cores, respectively. A fragment of apo B-100, denoted apo B-48, is found in chylomicrons, which transport dietary triacylglycerols and cholesteryl esters. The apo B-48 molecule is reported to correspond to the N-terminal 47 percent (residues 1–2142) of the apo B-100 molecule [Innerarity et al., J. Clin. Invest., 80:1794 (1987); Powell et al., Cell, 50:831 (1987); Chen et al., Eur. J. Biochem., 175:111 (1987)].

The complete amino acid residue sequence (4563 residues; 514 kDa) of human apo B-100, as determined by cDNA clones of hepatic mRNAs, has been reported [Knott et al., Nature 323:734 (1986); Knott et al., Nucl. Acids. Resch., 14:7501 (1986)]. The full cDNA sequence for the human apo B-100 gene, consisting of 29 exons, also has been reported [Ludwig et al., DNA 6:363 (1987)].

As the level of lipoproteins in circulation is related to the level of associated apoprotein, several schemes for assaying the apoprotein have been proposed. Immunoassays for native apo B-100 have been proposed which utilize specific antibody-containing antisera, including competitive fluid phase and solid phase radioimmunoassay (RIA), enzyme-linked immunosorbent assay (ELISA), and radial immunodiffusion (RID). Problems associated with these immunoassays include reproducibility and the homogeneity and specificity of the antisera used [Currey et al., Clin. Chem., 24:280–286 (1978); Rosseneu et al., Clin. Chem., 28:427–433 (1983); Albers et al. supra].

Several investigators have reported development of monoclonal antibodies against human B-100 apoproteins. The use of anti-apo B-100 monoclonal antibodies for measuring plasma B-100 levels has been proposed [Patton et al., Clin. Chem., 29:1898–1903 (1983); Maynard et al., Clin. Chem., 30:1620–1624 (1984); Young et al., Clin. Chem., 32:1484–1490 (1986); Young et al., Arteriosclerosis, 6:178 (1986)]. In addition, a mixture of anti-apo B-100 monoclonal antibodies in a RID assay for plasma B-100 has been proposed [Marconvina et al., Clin. Chim. Acta, 147:117–125 (1985)]. However, these assay techniques suffer from the requirements of lengthy incubations, repeated centrifugations and/or use of radioactive materials.

A number of antibody-binding domains of apo B-100 have been mapped with anti-apo B-100 antibodies [Knott et al., Nature 323:734 (1986); Krul et al., J.Lipid Res. 29:937 (1988); Pease et al., J.Biol.Chem. 265:553 (1990)]. In these studies, fragments of apo B-100 cDNA were cloned into vectors and expressed as $\beta$-galactosidase fusion proteins in E. coli. The fusion proteins were probed with various anti-apo B-100 antibodies. The results of these and other studies suggest that anti-apo B-100 monoclonal antibodies often recognize complex epitopes on native apo B-100 which are not recognized on delipidated apo B-100 [Curtiss et al., J. Biol. Chem., 257:15213 (1982)].

The antigenic heterogeneity of native apo B-100, as with apo A-I, is well documented. For instance, epitope expression on native apo B-100 molecules has been found to be modulated by: (1) the composition of associated lipids; (2) temperature of the immunoreaction; (3) the degree of isolation of LDL from its native environment; and (4) genetic variety among individuals. Thus, the identification of conserved, pan native epitopes of apo B-100 is important to any generally applicable assay method. An antibody composition that immunoreacts with a conserved, pan native apo B-100 epitope is similarly referred to as a pan antibody composition or pan antibodies.

Because of the unique specificity of monoclonal antibodies, their utility in an assay often depends upon the affinity of the antibodies for a target antigen. Moreover, although monoclonal antibodies may have sufficient liquid-phase affinity for an antigen, when the same antibodies are affixed to a surface they may not be as effective in binding the antigen. Hence, while certain monoclonal antibodies have been reported, their utility in a particular assay format must be demonstrated. Similarly, when an antigen such as LDL or other apo B-100-containing material is affixed to a surface the affinity of the immobilized material for antibodies in solution may not be sufficient, even though it is sufficient when the apo B-100-containing material is present in the liquid phase. See, e.g., Goding, J., *Monoclonal Antibodies: Principles and Practice*, Academic Press, New York (1983), pp 40–46.

Currently proposed methods for assaying the lipoproteins described above are deficient in a number of respects. For instance, immunoassay methods for determining the amount of native apo A-I in a lipoprotein-containing sample are disclosed in U.S. Pat. No. 4,677,057, U.S. Pat. No. 5,126,240 and U.S. Pat. No. 5,055,396. However, these methods do not disclose concurrent determination of other apoprotein levels. On the other hand, U.S. Pat. No. 4,828,986 proposes competitive and "sandwich" immunoassay methods for determining the ratio of apolipoproteins B-100 and A-I using monoclonal antibodies. However, the latter method does not permit assaying for apolipoproteins B-100 and A-I in the same sample aliquot.

Significantly, previously proposed assay methods require the use of "secondary" serum standards in order to make accurate determinations of the assayed apolipoproteins. As used herein, a "secondary standard" refers to: (1) delipidated lipoproteins with added native apoprotein; (2) truncated apoproteins; or (3) freshly isolated pooled plasma collected from normal donors, as described in U.S. Pat. No. 4,828,986. The frequent impracticability of using primary (native) standards is believed to be due to problems associated with their isolation, solubility, stability, and heterogeneity. A review of some of the problems associated with immunoassays of apolipoproteins is presented in Rosseneu et al., *Clin. Chem.*, 24:280–286 (1978); Albers et al., *Clinics in Laboratory Medicine*, (9)1:137 (1989).

Since the risk of coronary artery disease is known to be correlated to serum levels of HDL and LDL, which levels are related to apo A-I and apo B-100, respectively, an assay method that permits determination of both apoproteins is desired. Preferably, the apoprotein assays could be performed on a single sample aliquot. An assay method that permits ready calibration without the need for secondary serum standards is particularly desired.

SUMMARY OF THE INVENTION

The present invention relates to a nonnatural polypeptide that immunologically mimics a pan epitope present in native apo B-100 and in stored samples of that protein. Thus, a polypeptide of the invention immunoreacts with particular antibodies that are also immunoreactive with native apo B-100. Such a polypeptide is often referred to herein as a "subject polypeptide". A subject polypeptide is dispersible in aqueous media in the substantial absence of denaturing surfactants such as sodium dodecyl sulfate (SDS). Exemplary antibodies include polyclonal antisera to native apo B-100 and certain "pan" monoclonal antibodies, such as the antibodies secreted by hybridoma MB47, having ATCC Accession No. HB 8746.

A preferred dispersible polypeptide of the invention contains an amino acid residue sequence of apo B-100, as shown in SEQ ID NO:1 and in FIG. 1. Preferably, the apo B-100 sequence comprises about 80 up to about 375 residues as shown in the figure that includes amino acid residues about 3430 through about residue 3510, corresponding to residues 217 through 297 of SEQ ID NO:1. More preferably, the polypeptide contains an amino acid residue sequence of apo B-100 of about 90 through about 160 residues in length that includes residues about 3430 through about residue 3520, corresponding to residues 217 through 307 of SEQ ID NO:1. A particularly preferred subject polypeptide is a recombinant polypeptide that is expressed fused at the carboxy-terminus of another polypeptide or protein sequence.

In another aspect of the invention, a bifunctional apo A-I/B-100 fusion polypeptide that is dispersible in the substantial absence of denaturing surfactants is contemplated. The fusion polypeptide immunologically mimics both the before-described pan native apo B-100 epitope and a pan native apo A-I epitope. Thus, the fusion polypeptide can be regarded as a recombinant antigen that immunoreacts with antisera to a pan native apo B-100 epitope and antisera to a pan native apo A-I epitope, including monoclonal antibodies to these apoproteins.

Structurally, a dispersible apo A-I/B-100 fusion polypeptide of the invention contains:

(a) a first amino acid residue sequence of apo A-I as shown in SEQ ID NO:3 and in FIG. 2 that includes at least the amino acid sequence positions 120 through 135, with the fusion polypeptide also immunoreacting with pan anti-apo A-I antibodies, such as those secreted by a hybridoma selected from the group consisting of: AI-4 (ATCC HB 8744), AI-7 (ATCC HB 8745), AI-9 (ATCC HB 8741), AI-10 (ATCC HB 9200), AI-11 (ATCC HB 9201), AI-12 (ATCC HB 9202), AI-13 (ATCC HB 9203), AI-14 (ATCC HB 9204), and AI-18 (ATCC HB 9570); and (b) a second amino acid residue sequence of apo B-100 as shown in FIG. 1 from position about 3430 through about 3510, corresponding to residues 217 through 297 of SEQ ID NO:1, with the fusion polypeptide immunoreacting with pan anti-apo B-100 antibodies, such as those secreted by the hybridoma MB47 (ATCC HB 8746). The second amino acid residue sequence is operatively linked to the first amino acid residue sequence and constitutes the carboxy-terminal portion of the fusion polypeptide.

An apo A-I/B-100 fusion polypeptide contains an apo B-100 amino acid residue sequence described before for a subject polypeptide and an apo A-I amino acid residue sequence of about 15 up through about 250 residues in length. Also, the fusion polypeptide can have the apo A-I amino acid residue sequence linked to the apo B-100 sequence via a linking amino acid residue sequence containing one or more residues.

A subject apo A-I/B-100 fusion polypeptide thus contains a first amino acid residue sequence of apo A-I from about residue 120 through about residue 135 operatively linked to a second amino acid residue sequence that includes an apo B-100 sequence from about amino acid residue 3430 through about residue 3510. The former apo A-I sequence can be represented by the formula:

(SEQ ID NO: 5)
LysValGlnProTyrLeuAspAspPheGlnLysLysTrpGlnGluGlu,
1           5           10          15 as described more fully hereinafter. More preferably, an apo A-I/B-100 fusion polypeptide contains the amino acid residue sequence of apo B-100 from about residue 3430 through about residue 3520 operatively linked to the amino acid residue sequence of apo A-I from about residue 19 through about residue 250 of SEQ ID NO:3.

Most preferably, a subject fusion polypeptide has a beta-galactosidase moiety fused to the N-terminus of the polypeptide as an artifact of the cloning vector used for expression of the polypeptide. Thus, from N-terminus to C-terminus, a most preferred fusion protein contains the following order of amino acid residue sequences: beta-galactosidase apo A-I/apo B-100.

Also contemplated is an isolated DNA segment comprising a nucleotide sequence (SEQ ID NO:2) encoding an amino acid residue sequence of apo B-100 as shown in FIG. 1 including the sequence from about residue 3430 through about residue 3510, corresponding to residues 219 through 297 of SEQ ID NO:1 and nucleotides 649 through 891 of SEQ ID NO:2. The DNA segment preferably contains about 240 through about 1200, and more preferably about 295 through about 485, base pairs that encode an apo B-100 amino acid sequence.

Further contemplated is a self-replicating vector (recombinant DNA molecule) that comprises a before-described DNA segment encoding an amino acid residue sequence of apo B-100 as shown in FIG. 1 from about residue 3430 through about residue 3510. Preferably, a vector of the invention is transformed and expressed in the SURE ™ strain of E. coli. An exemplary vector in this regard encodes a beta-galactosidase amino acid residue sequence operatively linked to the apo B-100 sequence, as in a fusion protein.

A DNA segment encoding both a before-described apo B-100 polypeptide and an apo A-I polypeptide and an expression vector containing that DNA segment operatively ligated therein for expression is also contemplated as a recombinant DNA molecule. A particularly preferred DNA segment encodes a fusion polypeptide that includes an N-terminal beta-galactosidase, an apo A-I polypeptide described before and a C-terminal apo B-100 subject polypeptide.

A method for assaying a body fluid sample for its native apo B-100 content is also contemplated. Thus, one embodiment comprises a solid phase method for assaying the amount of native apo B-100 in a body fluid sample by competitive binding.

Here, in step (a) a predetermined amount of body fluid sample containing native apo B-100 is admixed in a liquid medium with a predetermined amount of a before-described dispersible subject apo B-100 polypeptide affixed to a solid support and a predetermined amount of pan anti-apo B-100 antibodies to form a solid-liquid admixture. The pan anti-apo B-100 antibodies immunoreact with the native apo B-100 of the sample and with the polypeptide.

The solid-liquid admixture is maintained under biological assay conditions for a time period sufficient for the pan anti-apo B-100 antibodies to immunoreact with the polypeptide to form a solid-phase polypeptide/anti-apo B-100 immunocomplex and with the native apo B-100 in the liquid phase to form an apo B-100/anti-apo B-100 immunocomplex in the liquid phase.

The amount of solid-phase polypeptide/anti-apo B-100 immunocomplex formed is determined, and thereby the amount of native apo B-100 in the body fluid sample is also determined.

Similarly contemplated is a method for assaying the amounts of native apo B-100 and native apo A-I in a body fluid sample. This method comprises the following steps.

(a) A predetermined amount of body fluid sample is mixed in a liquid medium with predetermined amounts of (i) a dispersible subject apo A-I/B-100 fusion polypeptide affixed to a solid support, (ii) pan anti-apo B-100 antibodies, and (iii) pan anti-apo A- antibodies to form a solid-liquid admixture. The anti-apo B-100 antibodies immunoreact with the native apo B-100 of the sample and the fusion polypeptide, and the anti-apo A-I antibodies immunoreact with the native apo A-I of the sample and the fusion polypeptide.

(b) The solid-liquid admixture is maintained under biological assay conditions for a time period sufficient for the anti-apo B-100 antibodies and anti-apo A-I antibodies to immunoreact with the fusion polypeptide and the liquid phase apo B-100 and apo A-I proteins to form solid phase-bound fusion polypeptide/anti-apo B-100 and fusion polypeptide/anti-apo A-I immunocomplexes and liquid phase apo B-100/anti-apo B-100 and apo A-I/anti-A-I immunocomplexes.

(c) The amounts of solid-phase fusion polypeptide/anti-apo B-100 and fusion polypeptide/anti-apo A-I immunocomplexes formed are determined, and thereby the amounts of native apo B-100 and native apo A-I in the sample are also determined.

Also contemplated is a method for assaying the amount of native apo B-100 in a body fluid sample that employs a subject polypeptide to inhibit the reaction of native apo B-100 with anti-apo B-100 antibodies. Here, the method comprises the following steps.

(a) A predetermined amount of body fluid sample containing native apo B-100 is admixed in a liquid medium with predetermined amounts of a dispersible subject polypeptide and solid phase-bound pan anti-apo B-100 antibodies to form an admixture, with the anti-apo B-100 antibodies immunoreacting with the native apo B-100 of the sample and with the polypeptide.

(b) The admixture is maintained under biological assay conditions for a time period sufficient for the anti-apo B-100 antibodies to immunoreact with the polypeptide and native apo B-100 to form a polypeptide/anti-apo B-100 immunocomplex and an apo B-100/anti-apo B-100 immunocomplex.

(c) The amount of polypeptide/anti-apo B-100 immunocomplex formed is determined, and thereby the amount of native apo B-100 in the body fluid sample is also determined.

Further contemplated is a method for standardizing an assay for the amount of native apo B-100 in a body fluid sample comprising:

(a) admixing a predetermined amount of body fluid sample containing native apo B-100 in a liquid medium with a predetermined amount of pan anti-apo B-100 antibodies to form a first admixture, the anti-apo B-100 antibodies immunoreactive with the native apo B-100 of the sample and with a before-described, subject apo B-100 polypeptide;

(b) maintaining the first admixture under biological assay conditions for a time period sufficient for the pan anti-apo B-100 antibodies to immunoreact with the native apo B-100 in the sample to form a native apo B-100/anti-apo B-100 immunocomplex;

(c) admixing a predetermined amount of the pan anti-apo B-100 antibodies in a liquid medium with a predetermined amount of a before-described, dispersible subject apo B-100 polypeptide to form a second admixture;

(d) maintaining the second admixture under biological assay conditions for a time period sufficient for the anti-apo B-100 antibodies to immunoreact with the polypeptide to form a polypeptide/anti-apo B-100 immunocomplex; and (e) determining the amount of native apo B-100/anti-apo B-100 immunocomplex formed and the amount of polypeptide/anti-apo B-100 immunocomplex formed, and thereby the amount of native apo B-100 in the body fluid sample.

Similarly contemplated is a method for standardizing an assay for the amounts of native apo B-100 and native apo A-I in a body fluid, as described hereinafter.

The present invention thus affords improved compositions and methods for assaying native apo B-100 levels, that are related to LDL cholesterol levels, in a body fluid sample. The present invention also affords improved compositions and methods for assaying native apo B-100 levels in conjunction with native apo A-I levels, the level of apo A-I being related to the HDL cholesterol levels. The immunoassays contemplated within the present invention can be performed more expeditiously and accurately than by current methods.

BRIEF DESCRIPTION OF THE DRAWINGS

FIG. 1 shown in four sheets (FIGS. 1A, 1B, 1C and 1D) depicts the amino acid residue sequence of human apo B-100, and its corresponding cDNA, from amino acid residue 3214 through residue 3590 according to the numbering scheme of Ludwig et al., *DNA*, 6:363 (1987). The amino acid residue sequence is also referred to herein as SEQ ID NO:1, and the DNA sequence is referred to herein as SEQ ID NO:2.

FIG. 2 shown in three sheets as FIGS. 2A, 2B and 2C illustrates the amino acid residue sequence of human apo A-I, including presignal (residues 1–18) and propeptide (residues 19–24) sequences, according to Seilhamer et al., *DNA*, 3(4):309 (1984). The corresponding "sense" cDNA strand for residues 1–267 is also presented. The amino acid residue sequence is also referred to herein as SEQ ID NO:3, with the DNA sequence being referred to as SEQ ID NO:4.

DETAILED DESCRIPTION OF THE INVENTION

A. Definitions

Amino Acid Residue Sequence: a series of two or more amino acid residues joined via peptide linkages between adjacent residues to form a peptide or polypeptide. An amino acid residue sequence is conveniently represented by the one or three letter abbreviations for its constituent amino acids. The abbreviations used herein for amino acids are those provided at 37 C.F.R. §1.822(b)(2) and are reproduced in the following table of correspondence:

| ABBREVIATION | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| J | Xaa | Unspecified |

The individual residues comprising an amino acid residue sequence herein may be in the D or L isomeric form as long as the desired functional property is retained by molecule(s) incorporating the amino acid residue sequence. Also, the amino acid residue sequence may include post-translationally modified amino acids, e.g., hydroxylated, glycosylated amino acid residues, or residues linked via disulfide bonds. In addition, an amino acid residue sequence can include one or more modified or unusual amino acids, such as those listed in 37 C.F.R. §1.822(b)(4), which are incorporated herein by reference. An amino acid residue sequence can be represented by the abbreviations corresponding to its constituent amino acids in which a hyphen between two adjacent abbreviations indicates a peptide linkage between the corresponding residues.

Antibody: a polypeptide that immunologically binds to a ligand group. Antibodies, as used herein, are immunoglobulin molecules and immunologically active fragments of immunoglobulin molecules. Such portions known in the art as Fab, Fab'; F(ab')$_2$ and F$\nu$ are included. Typically, antibodies bind ligands that range in size from about 6 through about 34 Å with association constants in the range of about $10^4$ to $10^{10}$ M$^{-1}$, and as high as $10^{13}$ M$^{-1}$. Antibodies can bind a wide range of ligands, including small molecules such as steroids and prostaglandins, biopolymers such as nucleic acids, proteins and polysaccharides, and synthetic polymers such as polypropylene. An "antibody combining site" is that structural portion of an antibody molecule comprised of a heavy and light chain variable and hypervariable regions that specifically binds (immunoreacts with) antigen. The term "immunoreact" in its various forms is used herein to refer to binding between an antigenic determinant-containing molecule (antigen) and a molecule containing an antibody combining site such as a whole antibody molecule or a portion thereof. An "antigenic determinant" is the structural portion of the antigen that is immunologically bound by an antibody combining site. The term is also used interchangeably with "epitope". Antibodies can bind a single epitope of an antigen (monoclonal) or multiple epitopes (polyclonal).

Fusion protein or polypeptide: A protein or polypeptide containing amino acid residue sequences from each of two distinct proteins; it is formed by the expression of a recombinant gene in which two coding sequences have been joined together such that their reading frames are in phase. A fusion protein results when the expressed material contains at least one complete protein sequence, whereas only portions of the proteins are present in a fusion polypeptide. Hybrid genes of this type may be constructed in vitro, e.g. in order to label the product of a particular gene with a protein which can be more readily assayed. For example, if a gene is fused to lacZ in *Escherichia coli*, a fusion protein or polypeptide with β-galactosidase activity or a partial sequence may be obtained. Alternatively, a protein may be linked to a signal peptide to allow its secretion by the cell.

Ligand: a molecule having a structural region that binds specifically to a particular receptor molecule, usually via electrostatic forces and/or hydrogen bonds. An exemplary receptor molecule is an antibody combining site.

Oligonucleotide/Polynucleotide/DNA Segment: a polymer of single or double stranded nucleotides. As used herein, these terms and their grammatical equivalents, can be composed of a naturally-occurring nucleic acid, e.g., adenine (A), cytosine (C), guanine (G), thymine (T), uracil (U), inosine (I), as well as a modified base, as presented at 37 C.F.R. §1.82(p)(1).

Peptide/Polypeptide: a polymer comprising at least two amino acid residues in which adjacent residues are connected by a peptide bond between the alpha-amino group of one residue and the alpha-carboxyl group of an adjacent residue. The primary structure of a polypeptide has a primary amine group at one terminus and a carboxylic acid group at the other terminus of the polymer. Thus, a polypeptide may be represented by the formula:

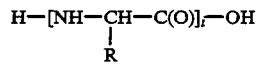

$$H-[NH-\underset{R}{CH}-C(O)]_i-OH$$

where R is a side chain characteristic of a given amino acid residue and i indicates the number of amino acid residues comprising the polymer which number is two or more. A polypeptide can comprise one or more amino acid residue sequences. Also, a polypeptide in aqueous solution is usually in one or more zwitterionic forms depending on the pH of the solution.

Protein: a single polypeptide or set of cross-linked polypeptides comprising more than about 50 amino acid residues. Proteins can have chemical crosslinking, e.g., via disulfide bridges, within the same polypeptide chain or between adjacent polypeptides. When a protein is glycosylated it may be called a glycoprotein. When a protein comprises one or more discrete polypeptide/protein subunits linked together, as by a peptide linkage, amino acid residue sequence, disulfide bridge, and the like, the protein is frequently termed a fusion protein, fusion polypeptide, chimeric fusion, and the like.

Receptor: a biologically active proteinaceous molecule having a structural region that specifically binds to (or with) another molecule (ligand). An antibody combining site is one type of receptor.

Vector: a DNA molecule capable of autonomous replication in a cell and to which a DNA segment, e.g., gene or polynucleotide, can be operatively linked so as to bring about replication of the attached segment. An expression vector is capable of directing expression of a DNA segment encoding one or more polypeptides such as when the DNA segment is under the control of a promoter sequence of the vector.

B. Polypeptides that Immunologically Mimic apo B-100

The present invention relates to an isolated polypeptide that immunologically mimics a pan immunologic binding region (epitope) of native apo B-100; i.e, the polypeptide immunoreacts with antibodies that immunoreact with at least 90 percent and more preferably at least 95 percent of radioiodinated apo B-100. A subject polypeptide mimics a single pan epitope of apo B-100. Moreover, a subject polypeptide can immunologically mimic one or more other apolipoprotein epitopes, such as a pan native apo A-I epitope, in addition to mimicking a pan native apo B-100 epitope.

Thus, a polypeptide is contemplated that mimics a plurality of apolipoprotein epitopes, including an apo B-100 epitope. When a polypeptide of the invention immunologically mimics more than one class of apolipoprotein, including apo B-100, the polypeptide at least immunoreacts with particular pan anti-apo B-100 antibodies, and also immunoreacts with antibodies immunoreactive with the other apolipoprotein.

A preferred polypeptide of the invention immunoreacts with pan anti-apo B-100 antibodies secreted by the hybridoma designated MB47, having ATCC Accession No. HB 8746. The monoclonal antibodies secreted by hybridoma MB47 are referred to herein as monoclonal MB47 antibodies or MB47 antibodies. MB47 antibodies immunoreact substantially identically both with freshly drawn apo B-100 and with stored samples that have partially decomposed. Thus, a subject polypeptide can be used as a long sought absolute immunological standard for apo B-100.

An exemplary polypeptide of the invention that immunoreacts with antibodies immunoreactive with more than one class of apolipoprotein is a fusion polypeptide immunoreactive with pan anti-apo B-100 antibodies and pan anti-apo A-I antibodies. Preferably, such a fusion polypeptide immunoreacts with MB47 antibodies as well as with pan anti-apo A-I antibodies secreted by the hybridoma designated AI-11, having ATCC Accession No. HB 9201.

A subject polypeptide that immunologically mimics native apo B-100 typically comprises an amino acid residue sequence identical to, or conservatively substituted from (as described hereinafter), a human apo B-100 amino acid residue sequence. Thus, a subject polypeptide can comprise a "truncated" amino acid residue sequence of apo B-100 up through about 375 amino acid residues in length, and includes an amino acid residue sequence that defines a pan antibody-binding region (epitope) of native apo B-100. A subject polypeptide can also include an immunologically "inert" spacing (linking) amino acid residue sequence, such as a β-galactosidase sequence (MW=1.1×10$^5$ Da; about 1200 residues), as long as the immunologically inert sequence does not substantially interfere with the immunological binding properties of the polypeptide; i.e., as immunologically inert, as described herein.

A subject polypeptide is dispersible (soluble) in an aqueous medium such as a usual buffer like PBS or bicarbonate in the substantial absence of a denaturing surfactant such as sodium dodecyl sulfate (SDS), polyoxyethylene(9)octylphenyl ether (Nonidet P-40 or Triton X-100), or the like. Small, non-denaturing amounts of such surfactants that do not interfere with binding of a fusion polypeptide to the surface of a plastic microtiter plate well can be present. Small molecule non-detergent denaturants such as urea, guanidine and 2-mercaptoethanol can be present in the dispersions.

As such, a subject polypeptide exemplifies an unexpected advantage over seemingly similar polypeptides known in the art such as those described in Pease et al., *J. Biol. Chem.*, 265:553–568 (1990), all of which are insoluble and require the presence of SDS even for use in Western blots. The required SDS dispersibility of those known polypeptides prevents their use in solid phase assays using plastic microtiter plates because the SDS inhibits binding of the polypeptide to the plastic solid phase microtiter plate well. SDS-containing aqueous dispersions of such insoluble materials are also turbid, viscous and cannot readily be pipetted. A subject polypeptide is therefore often referred to herein as dispersible or as a dispersible subject polypeptide.

A preferred polypeptide contains 80 residues through about 375 residues and includes the amino acid residue sequence of apo B-100 from about residue 3430 through about residue 3510 as shown in FIG. 1 corresponding to residues 217 through 297 of SEQ ID NO:1. A more preferred polypeptide contains 90 or more residues and includes an apo B-100 sequence from about position 3430 through about position 3520 corresponding to residues 217 through 307 of SEQ ID NO:1. Other preferred polypeptides include an amino acid residue sequence of apo B-100 as exemplified by sequences s1–s9 in Table 1 below.

TABLE 1

Selected Truncated Amino Acid and cDNA Sequences of apo B-100[1]

| No. | N-terminus[2] A.A.# | Nucl.# | C-terminus[2] A.A.# | Nucl.# | Sequence[3] Length | Relative MB47 Binding[4] |
|---|---|---|---|---|---|---|
| s1 | 3429 | 10287 | 3510 | 10530 | 81 | ++ |
| s2 | 3418 | 10254 | 3510 | 10530 | 92 | ++ |
| s3 | 3386 | 10158 | 3510 | 10530 | 124 | ++ |
| s4 | 3353 | 10059 | 3510 | 10530 | 157 | ++ |
| s5 | 3429 | 10287 | 3523 | 10569 | 94 | +++ |
| s6 | 3429 | 10287 | 3544 | 10632 | 115 | +++ |
| s7 | 3429 | 10287 | 3565 | 10695 | 136 | +++ |
| s8 | 3429 | 10287 | 3590 | 10770 | 161 | +++ |
| s9 | 3214 | 9642 | 3590 | 10770 | 376 | +++ |

[1]Sequence numbering scheme according to Ludwig et al. DNA, 6:363 (1987).
[2]A.A.# and Nucl.# are amino acid and nucleotide positions, respectively.
[3]The number of amino acid residues in the sequence is indicated.
[4]MB47 binding studies are described in Example 1.

The length and apo B-100 sequence positions of a subject polypeptide are of importance to the invention, as is discussed below.

An overlapping series of synthetic polypeptides, each containing 20 to 30 residues was prepared. The sequences of those polypeptides corresponded to the apo B-100 sequence from amino acid residue position 3416 through 3505. No binding was observed between any of the synthetic polypeptides and monoclonal MB47.

A further series of four expression polypeptides was also prepared each of which contained 15, 30, 37 or 53 amino acid residues and whose sequences corresponded to positions ending at position 3510 of the B-100 sequence. Assays using monoclonal MB47 also exhibited negative binding results.

Thus, even though there can be no disulfide bridges and no turn-inducing prolines in the region studied, the complete apo B-100 pan epitope bound by monoclonal MB47 appears to be non-linear and due to a folded, secondary and/or tertiary structure of the apo B-100 protein and a subject polypeptide. That epitope is mimicable by a polypeptide having an apo B-100 sequence that contains about 80 amino acid residues up through about 375 residues, more preferably up through about 160 residues, and includes an apo B-100 amino acid residue sequence from amino acid residue position about 3430 (about nucleotide position 10290) through about residue 3510 (about nucleotide position 10560). Polypeptides s1–s9 of Table 1 are exemplary of these polypeptides.

A more preferred polypeptide, also useful for assays or as a standard, is also present in a polypeptide containing about 90 through about 375 amino acid residues, and more preferably up through about 160 residues of the apo B-100 amino acid residue sequence from about residue position 3430 (about nucleotide position 10,290) through about residue position 3520 (about nucleotide position 10,570). This more preferred group includes polypeptides s5–s9 of Table 1.

A schematic that illustrates the relative lengths and positions of useful polypeptides s1–s8, as well as shorter recombinant apo B-100 amino acid sequence-containing polypeptides is provided below in Table 2.

TABLE 2

Schematic of Apo B-100 Sequence-Containing Polypeptides*

| Polypeptide Nucleotide Sequence Position | Polypeptide Designation of Table I | Relative MB47 Immuno-reactivity** |
|---|---|---|
| (10,059) 471 bp (10,530) | S4 | ++ |
| (10,158) 372 bp | S3 | ++ |
| (10,254) 276 bp | S2 | ++ |
| (10,287) 243 bp | S1 | ++ |
| (10,359) 171 bp | | — |
| (10,419) 111 bp | | — |
| (10,440) 90 bp | | — |
| (10,485) 45 bp | | — |
| (10,287) 483 bp (10,770) | S8 | +++ |
| 408 bp (10,695) | S7 | +++ |
| 345 bp (10,632) | S6 | +++ |
| 282 bp (10,569) | S5 | +++ |

*Parenthesized numbers are 5' and 3' positions in the apo B-100 gene shown in FIG. 1.
**Strong binding = +++; good binding = ++; no binding = —.

The results obtained herein are contrary to those reported in Table 1 of Pease et al., *J. Biol. Chem.*, 265:553–568 (1990). It should first be noted that those authors' results were obtained using Western blots with expressed polypeptides dispersible only in the presence of both 2-mercaptoethanol (2-ME) and sodium dodecyl sulfate (SDS).

Second, those authors identified the monoclonal MB47 epitope position at about residue 3506, whereas results with other monoclonals were reported to be in sequences having a length of about 75 through about 600 residues. An earlier report by the same research group [Knott et al., Nature, 323:734 (1986)] had placed the MB47 epitope near the carboxy-terminus of a recombinant β-galactosidase-apo-B-100 polypeptide containing amino acid residues 3350–3506. The present results with the 20–30-mer overlapping synthetic polypeptides discussed above, and particularly with a polypeptide spanning residues 3491–3510, as well as the results using the recombinants terminating at position 3510 (nucleotide position 10,530) indicate that monoclonal MB47 does not bind to a linear epitope at residue position about 3506. Rather, pan monoclonal MB47 binds to a conformational epitope that requires residues in the region of residue position 3430, as well as those in the region of positions 3510–3520.

Those earlier workers also found maximal binding to polypeptides containing about 400 residues at residue positions 3214–3611 and about 510 residues at positions 3214–3728, and poorer binding with a sequence of about 155 residues at residue positions 351–3506. That latter region and the region of a recombinant prepared herein encompassing amino acid residue positions 3349 through 3506 substantially encompass the sequence of polypeptide s5 (positions 3429–3523), which was found to exhibit maximal binding herein.

The present results therefore provide a surprising finding as to the length and positional requirements of the pan apo B-100 epitope bound by monoclonal MB47. Thus, a sequence of about 400 residues or more encompassing the B-100 sequence from residue position about 3430 through about 3520 plus added B-100 amino- and carboxyl-terminal residues can provide maximal MB47 binding in a Western blot and in the presence of SDS, as does a sequence of about 90 through about 375 residues in a solid phase assay in the substantial absence of SDS, whereas a polypeptide of about 155 residues whose sequence was displaced only about 15 residues toward the amino-terminus from residue about 3520 provided poorer, unacceptable binding in a Western blot. Still further, Pease et al. found a polypeptide of about 360 residues whose carboxy-terminus was about 25 residues toward the amino-terminus from residue position 3420 showed minimal to no Western blot binding (binding reported as ± as compared to ++ for the 400-mer above) with monoclonal MB47.

Preferably, a subject polypeptide is recombinantly expressed in the SURE ™ strain of *Escherichia coli*. Thus, a preferred subject polypeptide, which immunologically mimics only the pan native apo B-100 apolipoprotein epitope, is expressed by SURE ™ *E. coli* transformed with a vector encoding the polypeptide. A preferred polypeptide in this regard is expressed by SURE ™ *E. coli* transformed with the plasmid designated "84", which plasmid encodes polypeptide s4 of Table 1. A more preferred polypeptide is also expressed by SURE ™ *E. coli* transformed with the plasmid designated "144" which plasmid encodes polypeptide s5 of Table 1. These and other plasmids are discussed in greater detail hereinafter.

As mentioned before, another aspect of the present invention is a dispersible fusion polypeptide, or a fusion protein, that immunologically mimics native apo B-100 and native apo A-I. The entire apo A-I amino acid residue sequence can be operatively linked to a before-described apo B-100 sequence, making the linked construct a fusion protein, or an apo A-I polypeptide sequence of less than the entire apo A-I length can be used, making the operatively linked construct a fusion polypeptide. Thus, such a fusion polypeptide or protein immunoreacts with pan anti-apo B-100 antibodies as well as with pan anti-apo A-I antibodies. For convenience of expression, a fusion protein will often hereinafter be referred to as a fusion polypeptide.

As is discussed elsewhere, a recombinant polypeptide that immunologically mimics only the pan apo B-100 epitope can also be expressed operatively linked to all or part of the amino acid sequence of another immunologically inert protein, and therefore also be a fusion polypeptide or fusion protein. To distinguish constructs containing only an apo B-100 epitope from those containing both apo B-100 and apo A-I epitopes, as the relevant epitopes, the former will hereinafter be generally referred to as an apo B-100 fusion polypeptide, and the latter as an apo A-I/B-100 fusion polypeptide.

A contemplated fusion polypeptide immunoreacts with anti-B-100 MB47 monoclonal antibodies. Still more preferred is a fusion polypeptide that includes the apo A-I amino acid residue sequence from position about 120 through about 135 (the pan epitope) and also immunoreacts with pan anti-apo A-I monoclonal antibodies secreted by hybridoma AI-11 (ATCC HB 9201). An apo A-I-containing fusion polypeptide can also preferably immunoreact with monoclonal antibodies secreted by a hybridoma selected from the group consisting of:

|  | Deposit Date |
|---|---|
| AI-4 (ATCC HB 8744), | 3/5/85 |
| AI-7 (ATCC HB 8745), | 3/5/85 |
| AI-9 (ATCC HB 8741), | 3/5/85 |
| AI-10 (ATCC HB 9200), | 9/16/86 |
| AI-12 (ATCC HB 9202), | 9/16/86 |
| AI-13 (ATCC HB 9203), | 9/16/86 |
| AI-14 (ATCC HB 9204), | 9/16/84 |
| AI-18 (ATCC HB 9570), | 10/14/87 | which hybridomas along with MB47 (deposited Mar. 3/6/85), AI-11 (deposited 9/16/86) and MB24 (deposited 3/6/85) have been deposited with the ATCC pursuant to the Budapest Treaty.

A pan native epitope of either apo B-100 or apo A-I can thus be defined by immunoreaction with an appropriate monoclonal antibody such as MB47 or AI-11, respectively. A pan anti-apo B-100 antibody or a pan anti-apo A-I antibody immunoreacts with at least 90 percent, and preferably at least 95 percent of $^{125}$I-labeled apo B-100 or apo A-I, respectively.

A subject polypeptide referred to herein as an apo A-I/B-100 fusion polypeptide is dispersible as discussed previously, and comprises a first amino acid residue sequence that includes an amino acid residue sequence of a pan apo A-I epitope operatively linked to a second amino acid residue sequence that includes an amino acid residue sequence of a pan apo B-100 epitope. An amino acid residue sequence is said to be "operatively linked" to a second amino acid residue sequence when the sequences are joined by one or more covalent bonds, as by a direct peptide bond, disulfide bond, or by an intervening peptide-bonded linking amino acid residue sequence. Preferably, the first and second amino acid residue sequences are linked together via a peptide-bonded third amino acid residue sequence of one or more residues.

A fusion polypeptide of the invention preferably includes a pan apo B-100 amino acid residue sequence as listed in Table 1 above. Thus, a preferred apo A-I/B-100 fusion polypeptide includes a truncated apo B-100 sequence listed in Table 1 operatively linked at the carboxy-terminus of an amino acid residue sequence of apo A-I that defines a pan epitope of that molecule; i.e., residues 120 through 135. A particularly preferred apo A-I/B-100 fusion polypeptide includes an amino acid residue sequence of apo A-I as shown in SEQ ID NO:3 and FIG. 2. The apo A-I sequence is according to Seilhamer et al., *DNA*, 3(4):309 (1984).

A fusion polypeptide of the invention is sufficiently long to permit the polypeptide to display the immunologic activities described before. Hence, the length of a particular polypeptide of the invention depends upon the immunologic activities desired. The pan apo B-100 and apo A-I epitopes of a fusion polypeptide are arrayed such that immunoreaction of pan anti-apo B-100 antibodies is substantially independent of immunoreaction of pan anti-apo A-I antibodies.

As a preferred fusion polypeptide is an apo A-I/B-100 polypeptide comprising an amino acid residue sequence of a pan apo B-100 epitope operatively linked to the carboxy-terminus of an amino acid residue sequence of apo A-I that includes a pan epitope, the length of the fusion polypeptide is determined by the lengths of its respective pan apo B-100 and pan apo A-I epitopes, and, optionally, linking amino acid residue sequences that can be present. In a preferred apo A-I/B-100 fusion polypeptide, a pan apo B-100 sequence (e.g., s1 in Table 1) containing 82 residues is joined to the carboxy-terminus of a pan apo A-I sequence epitope containing the noted sixteen residues via a linking sequence of about 120 residues of the apo A-I sequence.

A more preferred apo A-I/B-100 fusion polypeptide includes an amino acid residue sequence of apo B-100 from about residue 3430 through about residue 3520 (e.g., s5 in Table 1) operatively linked via a linking amino acid residue sequence to an amino acid residue sequence of apo A-I as shown in FIG. 2 from about residue 120 through about residue 135 therein. That latter apo A-I sequence is represented by the amino acid residue sequence:

(SEQ ID NO: 5)
LysValGlnProTyrLeuAspAspPheGlnLysLysTrpGlnGluGlu
1       5           10              15

A particularly preferred apo A-I/B-100 fusion polypeptide of the invention includes the amino acid residue sequence from residue 3429 (about 3030) to residue 3523 (about 3520; s5 in Table 1) of apo B-100 linked via a peptide bond to the C-terminal end of the apo A-I amino acid residue sequence from residue 19 through residue 240. Thus, the apo A-I sequence from residue 121 through residue 240 can also be viewed as an about 120 amino acid residue linking sequence. Such a fusion polypeptide is synthesized by the plasmid designated "137" when transformed and expressed in SURE ™ *E. coli*, details of which are described hereinafter.

Exemplary linking sequences are formed by expression of nucleotide sequences that are utilized for restriction endonuclease cleavage of DNA molecules used to construct the recombinant molecules that express an apo B-100 fusion polypeptide or apo A-I/B-100 fusion polypeptide or protein. Blunted restriction sites can also give rise to linking amino acid residue sequences upon ligation into a recombinant DNA molecule (as discussed hereinafter) and expression. Amino acid residue sequences of apo B-100 and apo A-I in addition to those of a pan epitope can also be included as a linking sequence. Another exemplary linking sequence is Gly-GlyGlyGlySer (SEQ ID NO:6), whose encoding DNA can be ligated between an apo A-I- and a B-100-encoding DNA sequence.

It should be apparent to any worker skilled in molecular biology that substantially any polypeptide can be used as a linking sequence so long as it is immunologically inert, as described herein, and so long as it is free of residues such as cysteines and residues such as tryptophans, phenylalanines and the like that can cause insolubilization (non-dispersibility in the substantial absence of SDS) of the expressed material or otherwise inhibit its immunoreactivity. A linking sequence, also sometimes referred to herein as a spacing sequence, can contain one residue up through about 1200 residues as is the case when a fusion polypeptide or fusion protein is expressed linked to the carboxy-terminus of β-galactosidase.

The apo B-100 sequence of an instant fusion polypeptide is located proximate the carboxy-terminus of the molecule so that the N-terminus of the apo B-100 sequence is linked to the C-terminus of the other, non-apo B-100 sequence such as β-galactosidase. This preference stems from diminished monoclonal MB47 binding that was observed when the order of two sequences in the expressed fusion polypeptide were reversed. Thus, when an apo B-100 epitope is placed at the carboxy-terminus binding as noted in Table 1 is observed, whereas when at the amino-terminus of an apo A-I epitope, binding was questionable (+ + + or + + vs ±).

Accordingly, an apo A-I/B-100 fusion polypeptide has an apo A-I amino acid residue sequence located proximate the amino-terminus of the fusion polypeptide.

It is noted that the N-terminal apoprotein sequence usually is linked to another, linking, immunologically inert amino acid residue sequence, which extends to the amino-terminus of the complete expressed polypeptide molecule. The linking amino acid residue sequence is typically an artifact of the expression system employed to synthesize the polypeptide and is immunologically "inert", i.e., it does not substantially interfere with the ability of the fusion polypeptide to immunoreact with pan anti-apolipoprotein antibodies. An exemplary immunologically "inert" amino acid residue sequence in this regard is a β-galactosidase moiety as generated by a pUR expression vector.

When an amino acid residue sequence other than those of a pan apo B-100 epitope or a pan apo A-I epitope is provided at the N-terminus of a subject polypeptide, the resulting molecule is itself a fusion polypeptide even though it may contain only one of the apo A-I or apo B-100 epitope amino acid residue sequences. The N-terminal linking sequence in this case is preferably immunologically inert.

However, a linking sequence can in certain embodiments inhibit the interaction of the polypeptide with antibodies to the polypeptide. In the latter case, it is preferred that the interfering region of the polypeptide, which causes the inhibition, is cleavable from the targeted region of the molecule.

Cleavage of the interfering region can be facilitated by the introduction of a "hinge" region into the molecule. The hinge region defines a cleavage site between the N-terminal sequence desired to be cleaved and the targeted region of the polypeptide. Methods for introducing such a hinge region into a fusion polypeptide are described in U.S. Pat. No. 5,013,653, the disclosure of which is incorporated herein by reference.

From a different vantage, a subject polypeptide, including a fusion polypeptide, is conveniently represented by the following formula:

wherein:

$A_i$, when present, represents a pan apo A-I epitope amino acid residue sequence, and B represents a pan apo B-100 epitope amino acid residue sequence; and $S_w$ and $S_x$, when present, each represents a spacing (linking) immunologically inert amino acid residue sequence. Each of variables i, w and x, can vary independently of each other and can equal zero or one. When a variable is equal to zero, the amino acid residue sequence with which it is associated (to the left side) is absent; and when a variable is equal to one, the sequence with which it is associated is present.

Thus, at least a before-described apo B-100 polypeptide that contains a monoclonal MB47-binding epitope is present, and a before-defined amino acid residue sequence of apo A-I can also be present. When an "S" amino acid residue sequence is present in a fusion polypeptide, as represented by the above formula, the "S" sequence is as defined hereinbefore for a linking amino acid residue sequence, which can also include a portion of an immunologically inert, protein that is an artifact of expression.

Accordingly, a particularly preferred fusion polypeptide, an apo A-I/B-100 fusion polypeptide, has i=1 wherein the "$A_i$" sequence closer to the N-terminus (H) of the molecule is an amino acid residue sequence of apo A-I containing a pan epitope, and the B sequence closer to the C-terminus (OH) of the molecule is an amino acid residue sequence of a subject apo B-100 polypeptide discussed before. Also, a preferred apo A-I/B-100 fusion polypeptide has w=1 and x=1 in which case the "S" sequence, $S_w$, includes an amino acid residue sequence of β-galactosidase, present as an artifact of expressing the fusion polypeptide from a pUR291 plasmid vector, and $S_x$ is an artifact due to restriction sites or their residual bases used in creating the expression vector, as described hereinafter.

Typically a subject polypeptide, including a fusion polypeptide, is not glycosylated; i.e., as when it is expressed by a prokaryotic host. However, a polypeptide of the invention can be eukaryotically produced, in which case it may be glycosylated. Also, a subject polypeptide can incorporate a variety of changes, such as insertions, deletions, and conservative substitutions of amino acid residues as can be present in allelic variants, as long as the resulting molecule exhibits the desired properties. The "desired properties" as referred to herein include that the modified polypeptide has the same or similar dispersibility and immunoreactive properties as those for the unaltered polypeptide, as described hereinbefore.

When an instant polypeptide incorporates a conservative substitution in an amino acid residue sequence including the sequences presented above, the substituted amino acid residue is replaced by another, biologically similar amino acid residue such that the resulting polypeptide has an amino acid residue sequence that is compositionally different from the unsubstituted amino acid residue sequence. Some contemplated examples of conservative substitutions include substitution of a hydrophobic residue such as isoleucine, valine, leucine or methionine for another hydrophobic residue. Also, a polar residue such as arginine, lysine, glutamic acid, aspartic acid, glutamine, asparagine, and the like, can be conservatively substituted for another member of this group.

Still another aspect of a polypeptide incorporating conservative substitutions occurs when a substituted amino acid residue replaces an unsubstituted parent amino acid residue. Examples of substituted amino acids can be found at 37 C.F.R. §1.822(b)(4), which species are incorporated herein by reference. When a subject polypeptide has an amino acid residue sequence corresponding to the sequence for a native apoprotein, but for one or more conservative substitutions, preferably no more than about 40 percent, and more preferably no more than about 20 percent, of the amino acid residues of the native apoprotein are substituted in the polypeptide.

A subject polypeptide incorporating one or more conservative substitutions can immunologically mimic a natural allelic variant of a native apolipoprotein discussed hereinbefore. Thus, an immunologic probe is contemplated in an assay for the allelic variant.

A polypeptide of the present invention can be synthesized by any of the peptide synthetic techniques known to those skilled in the art. A summary of some of the techniques available can be found in J. M. Stuard and J. D. Young, "Solid Phase Peptide Synthesis", W. H. Freeman, Co , San Francisco (1969), J. Meinhofer, "Hormonal Proteins and Peptides" Vol. 2, pp. 46, Academic Press (New York) 1983, and U.S. Pat. No. 4,631,211, which description is incorporated herein by reference. These techniques usually employ a solid phase technique such as that described in Merrifield, *JACS*, 85:2149 (1963). Alternatively, a subject polypeptide can be prepared by direct coupling of two smaller polypeptides, e.g., via a peptide linkage or disulfide bridge.

Preferably, however, a subject polypeptide is synthesized by recombinant DNA techniques. Such recombinant techniques are favored especially when the desired polypeptide is relatively long, e.g., more than about 50 residues in length, as is the case here for an apo B-100 polypeptide. When recombinant DNA techniques are employed to prepare a subject polypeptide, a DNA segment coding for the desired polypeptide or precursor to the polypeptide is ligated to a preselected vector for subsequent expression.

A preferred subject polypeptide is expressed by the SURE TM *E. coli* cell line (Stratagene Cloning Systems; La Jolla, Calif.). Thus, a conservatively substituted polypeptide incorporating any post-translation modifications effected by SURE TM *E. coli* cells is also contemplated. Accordingly, a subject polypeptide can be expressed by SURE TM *E. coli* transfected with plasmid "84" or "144" which plasmids have a molecular weight of about 6 Kb (kilobases) as determined by agarose gel electrophoresis, can have an amino acid residue sequence conservatively substituted from that described before. A subject apo A-I/B-100 fusion polypeptide can be expressed by SURE TM *E. coli* transfected with plasmid "137", which plasmid has a molecular weight of about 6.6 Kb as determined by agarose gel electrophoresis.

C. DNA Segments

A DNA segment of the invention (a subject DNA segment) encodes a before-described subject polypeptide. A subject DNA segment is contemplated to be a discrete, "isolated" chemical species available for manipulation, as when generated by the polymerase chain reaction (PCR), as described below. All DNA segments discussed herein have both 5' and 3' ends.

Alternatively, an isolated, subject DNA segment can be operatively ligated to a vector, as when it is to be cloned or subsequently expressed in a suitable host. The DNA segment is "operatively ligated" to a vector when it is covalently bonded in-frame for expression of a subject polypeptide or fusion polypeptide to the vector, as is well known. Additionally, when the DNA segment is operatively ligated to an expression vector, a promoter sequence is present so that expression of the DNA segment is under the control of the promoter sequence. Vectors containing an operatively ligated subject DNA segment are discussed in greater detail hereinafter.

A preferred isolated DNA segment comprises a nucleotide sequence of at least 240 base pairs encoding a subject polypeptide, such as the amino acid residue sequence of apo B-100 shown in FIG. 1 from about residue 3430 through about residue 3510 (e.g., the 243 bp DNA that encodes polypeptide s1 in Tables 1 or 2). The nucleotide sequence encoding the apo B-100 amino acid residue sequence can include up through about 1130 nucleotide base pairs of the apo B-100 sequence shown in SEQ ID NO:2, such as the about 1130 bp segment used to express polypeptide s9. Preferably, the apo B-100 isolated DNA segment encodes an amino acid residue sequence which is one listed in Table 1, before, and the DNA segment comprises a nucleotide sequence from the positions therein. A particularly preferred isolated DNA segment encodes apo B-100 epitope polypeptide s5, s6, s7, s8 or s9.

Also contemplated is an isolated DNA segment that encodes an amino acid residue sequence of apo A-I shown in SEQ ID NO:4 and FIG. 2, including the sequence from amino acid residue 120 to residue 135: LysValGlnProTyrLeuAspAspPheGlnLysLysTrpGlnGluGlu (SEQ ID NO:5). More preferably, the entire DNA segment comprises up through about 696 nucleotides and encodes an amino acid residue sequence of apo A-I as shown in FIG. 2 that encompasses the entire apo A-I molecule. Most preferably, an apo A-I-encoding DNA having about 663 bp that encodes amino acid residue positions from about residue 19 through residue 240. Any non-apo A-I residues can be selected from the full set of amino acid residues defined hereinbefore, with the previously noted caveat as to non-inhibition with the immunoreactivity of the expressed polypeptide.

An above-described DNA segment encoding an amino acid residue sequence of one apolipoprotein can also be operatively ligated; i.e., ligated in-frame, to another DNA segment encoding a different apolipoprotein. Thus, a DNA segment comprising nucleotide sequences encoding a pan apo B-100 epitope sequence as well as a pan apo A-I epitope sequence is contemplated. A particularly preferred DNA segment containing both a pan apo B-100 epitope sequence and a pan apo A-I DNA epitope sequence is present in plasmid "137" and can be isolated as an approximately 1150–1160 bp restriction fragment having a BamHI, SalI or PstI restriction site (as are present in the polylinker of plasmid vector pUR291 discussed hereinafter) at the 5' end and a Pst I site at the 3' end. It is to be understood that longer DNA segments are contemplated as where DNA encoding polypeptides s6–s9 are utilized along with the 663 bp apo A-I DNA, as are shorter DNA segments as where a DNA segment coding for polypeptide s5 is used along with apo A-I DNA coding for the apo A-I polypeptide from residue 120 through residue 135 discussed above.

A subject isolated DNA segment or that segment ligated into a vector as a recombinant DNA molecule discussed hereinafter can also include codons that encode amino acid residues other than those of an apo B-100 or apo A-I sequence. Those other codons and encoded amino acid residues of an expressed polypeptide constitute the previously discussed spacing (linking) sequence of an $S_{w-x}$ of the previously discussed equation.

Thus, a subject polypeptide of the previously discussed formula can be encoded by a subject isolated DNA segment. Frequently, as in the case of an expressed fusion polypeptide, the $S_w$ portion of the previous formula is contributed by the vector, although by appropriate selection of vectors and restriction sites, an isolated DNA segment of the invention can also encode a desired polypeptide without the spacing amino residue sequence $S_w$.

The total length of an isolated DNA segment of the invention is mostly a matter of choice once at least a before-mentioned pan apo B-100 epitope-encoding sequence is present. For example, one to several thousand base pairs can be present downstream of the expression stop codon. Similarly, one to one thousand or more base pairs can be present upstream from the apo B-100 epitope expression start codon, so long as the expression frame is maintained, as where a subject DNA segment includes codons for an apo B-100 epitope as well as a portion of the β-gal gene and the regulatory sequences for the β-gal gene.

A minimal length for such a segment is about 280 bp that encodes polypeptide s1 and the before-described 16-mer apo A-I polypeptide from amino acid residue position 120 to position 135. As a polypeptide s5–s9 is a more preferred apo B-100 polypeptide, a more preferred DNA segment at least contains a polypeptide s5-encoding sequence of about 280 bp or more preferably still the s8-encoding sequence of about 480 bp plus the 663 bp that encode the apo A-I amino acid residue sequence discussed before. The presence of additional base pairs is also contemplated for linking sequence, as discussed before.

An RNA segment equivalent (complementary) to a DNA segment described above is also contemplated. In this embodiment, an RNA segment can be ligated to an RNA vector, e.g., viral RNA, as is well known.

A subject DNA segment can be readily synthesized by chemical techniques, e.g., by the well-known phosphotriester method [Matteuci et al., *JACS*, 103:3185 (1981)]. By chemically synthesizing the DNA segments, any desired substitution, insertion or deletion of an amino acid residue or sequence from a template polypeptide can be readily provided by making the corresponding change in the nucleotide sequence of the DNA segment.

In addition to synthetic chemical techniques, a DNA segment of the invention can be produced by enzymatic techniques. Thus, restriction enzymes, which cleave DNA molecules at predefined recognition sequences, can be used to isolate DNA fragments from larger DNA molecules that encode a subject polypeptide. Typically, DNA fragments produced in this manner have cohesive, "overhanging" termini, whereby single-stranded nucleotide sequences extend beyond the double-stranded region of the molecule. The presence of such cohesive termini is often preferred over blunt-ended DNA molecules, although blunt-ended DNA can be used as can fragments having one blunt end and one overhanging end. The isolated DNA fragments can then be operatively ligated (cloned) into a suitable vector, thereby incorporating the subject DNA segment into the vector.

Whenever an RNA segment coding for a subject polypeptide is used, an RNA molecule including the RNA segment is transcribed into complementary DNA (cDNA) via a reverse transcriptase. The cDNA molecule can then be ligated to an expression vector which can be transfected in a suitable host to give the desired subject polypeptide.

A DNA segment coding for an above-described amino acid residue sequence can be provided with start and stop codons or one or both of the start and stop codons can be provided by the larger DNA molecule, e.g., vector, operatively ligated to the DNA segment. A desired polypeptide of the invention can be prepared by judicious placement of the start and stop codons. For instance, a nucleotide sequence can be provided at one or both of the 3' and 5' ends of the DNA segment so that a polypeptide is expressed which is larger than a pan epitope amino acid residue sequence discussed before by inclusion of an N-terminal or C-terminal amino acid residue sequence. Additionally, it is contemplated that regulator, promoter and operator loci can be provided at the 5' end of a subject DNA segment as desired.

In addition to standard chemical or enzymatic synthetic techniques, an instant DNA segment can be generated using a polymerase chain reaction (PCR) protocol. In PCR, a specific polynucleic acid target is transcribed by a reaction in which a primer molecule complementary to a particular section of a nucleic acid template is used to form an extension product of the primer including a nucleic acid region complementary to the target. After separation of template and extended primer, each primer extension product acts as a template and specifically anneals with a complementary primer molecule. The resulting primed template acts as a substrate for further extension reactions. These steps are repeated, preferably using an automated cycling procedure, thereby exponentially amplifying the initial polynucleic acid target to which the primer hybridizes. Procedures for conducting PCR have been extensively described, see, e.g., U.S. Pat. Nos. 4,683,195 and 4,683,202, which descriptions are incorporated herein by reference.

As a target DNA segment frequently is present only in very small quantities, PCR affords sufficient amplification of the target DNA segment to permit efficient cloning and expression of the targeted segment. For instance, plasmids previously cloned with an apo B-100 cDNA segment that includes the targeted template DNA region can be used in PCR. A subject DNA segment can thereby be generated as a discrete species.

A preferred template plasmid coding for the 3214 to 3727 amino acid residue sequence of apo B-100 is designated "1.5 Kb" and is available from Dr. Stephen Young of the Gladstone Foundation Laboratories, San Francisco, Calif. The "1.5 Kb" plasmid is also described by Pease et al., *J.Biol.Chem.*, 265:553 (1990). A preferred template plasmid coding for the entire amino acid residue sequence of apo A-I is designated "0.6 Kb" and is available from Dr. Jan Breslow, Rockefeller University, New York, N.Y. and from the American Type Culture Collection (ATCC) under Accession No. 57025.

As PCR employs forward and reverse single stranded oligonucleotide primer molecules to initiate the polymerization reaction at each amplification stage, forward and reverse primer molecules complementary to at least a portion of the target DNA segment are contemplated. Also contemplated are primer molecules having a nucleotide sequence that defines a recognition sequence of a preselected restriction enzyme which flanks the region of the primer molecule complementary to the target DNA segment.

The primer must be sufficiently long to prime the synthesis of extension products in the presence of the agents for polymerization. The exact lengths of the primers depend on many factors, including temperature and the source of primer. For example, depending on the complexity of the template sequence, a polynucleotide primer typically contains 15 to 25 or more nucleotides, although it can contain fewer nucleotides. As few as 8 nucleotides in a polynucleotide primer have been reported as effective for use [Studier et al, *Proc. Natl. Acad. Sci. USA*, 86:6917–21 (1989)]. Short primer molecules generally require lower temperatures to form sufficiently stable hybridization complexes with template to initiate primer extension.

Forward (F) and reverse (R) primers that can be used to generate a cDNA segment coding for an above-described apo B-100 amino acid residue sequence from a "1.5 Kb" template are depicted below in Table 3. Preferred pairs of forward and reverse primers for generating a particular DNA segment are indicated in Table 4, thereafter, along with the number of the resulting plasmid in which the PCR-prepared DNAs was ligated. The primers are selected so as to define a PstI, BamHI or XhoI restriction site on either side of the targeted DNA segment.

TABLE 3

Useful Apo B-100 Primers

| Primer No.* | Sequence |
|---|---|
| 37F | (10,059) <br> 5' ATGC GGATCC <u>AAA</u>TTAGAGGGCACCACAAGA 3' <br> (BamHI) <br> (SEQ ID NO:7) |
| 34F | (10,158) <br> 5' ATGC GGATCC <u>AC</u>TGTGAGCTTAACCACGAAA 3' <br> (BamHI) <br> (SEQ ID NO:8) |

TABLE 3-continued

Useful Apo B-100 Primers

| Primer No.* | Sequence |
|---|---|
| 33F | (10,254)<br>5' ATGC GGATCC AATGAATACCAAGTCAAAA 3'<br>(BamHI)<br>(SEQ ID NO:9) |
| 46F | (10,287)<br>5' ATGC GGATCC TCCTCCATGGAATTTAAGTATGAT 3'<br>(BamHI)<br>(SEQ ID NO:10) |
| 132F | (10,287)<br>5' ATGC CTCGAG TCCTCCATGGAATTTAAGTATGAT 3'<br>(XhoI)<br>(SEQ ID NO:11) |
| 99R | (10,530)<br>5' ATAG CTGCAG TTTGGAAGTGCCCTGGAGCTTCACTG<br>(PstI)<br>AGACCG 3'<br>(SEQ ID NO:12) |
| 130R | (10,770)<br>5' TTAA CTGCAG CTATTA GCCAAGGTCAGGGAAATCATG 3'<br>(PstI)   stop<br>(SEQ ID NO:13) |
| 133R | (10,695)<br>5' AATT CTGCAG TTATCA GCCGGGAGAGAGTTCCAGGGT 3'<br>(PstI)   stop<br>(SEQ ID NO:14) |
| 134R | (10,632)<br>5' AATT CTGCAG TTATCA GTGTAAGTGGTTTTTCGTACT 3'<br>(PstI)   stop<br>(SEQ ID NO:15) |
| 135R | (10,569)<br>5' AATT CTGCAG TTATCA AAAATTTTCTTTTACTTCAAG 3'<br>(PstI)   stop<br>(SEQ ID NO:16) |

*A primer designated with a number plus "F" is a forward primer, whereas a primer designated with a number plus "R" is a reverse primer. Sequence numbering is as in Table 1. Restriction sites are named in parentheses beneath each sequence.

TABLE 4

Apo B-100 Primers and Plasmid Numbers

| Primers<br>(Forward/Reverse) | Plasmid<br>Number | B-100 Coding<br>Positions | Peptide<br>Number |
|---|---|---|---|
| 37F/99R | 84 | 10,059–10,530 | s4 |
| 34F/99R | 83 | 10,158–10,530 | s3 |
| 33F/99R | 82 | 10,254–10,530 | s2 |
| 46F/99R | 97 | 10,287–10,530 | s1 |
| 46F/130R | 127 | 10,287–10,770 | s8 |
| 46F/133R | 146 | 10,287–10,695 | s7 |
| 46F/134R | 145 | 10,287–10,632 | s6 |
| 46F/135R | 144 | 10,287–10,569 | s5 |

The primers used herein are selected to be substantially complementary to the strands of each sequence to be amplified. Accordingly, the primer contains a nucleotide sequence sufficiently complementary to non-randomly hybridize with its respective template strand. Therefore, the hybridizing region of the primer sequence may not be exactly complementary with the template.

For example, a non-complementary polynucleotide can be attached to the 5' end of the primer, with the remainder of the primer sequence being substantially complementary to the strand. Such noncomplementary polynucleotide can code for a site for protein binding or permit adjustment of the reading frame of the codons. Also, a noncomplementary base can be interspersed in the primer, provided the primer sequence has sufficient complementarity with the sequence of the template strand to allow non-random hybridization to take place under hybridizing conditions, e.g., as when an inosine base is used for nonspecific coding. Primers having as little as a three-nucleotide exact match at the 3' end of the primer can be capable of specifically initiating primer extension products [Sommer, et al., Nuc. Acid Res., 17:6749 (1989)].

Preferably, the primer is provided in single-stranded form for maximum efficiency, but it can be double-stranded. If a double-stranded primer is used, the primer is first melted to separate its strands before being used to prepare extension products. Preferably, the primer is a polydeoxyribonucleotide.

Primers can be prepared by a variety of methods including de novo chemical synthesis and derivation of nucleic acid fragments from native nucleic acid sequences such as genes, alleles, introns, and codons of a genome, plasmid, or vector. Fragments can be obtained by such methods as restriction endonuclease limit digest of larger double-stranded nucleic acids and polymeric synthesis using a polymerase and a nucleic acid template. De novo chemical synthesis of a polynucleotide is generally preferred when a native DNA sequence coding for a subject polypeptide is known and can be conducted using any suitable method, such as the well-known phosphotriester or phosphodiester methods. See, for example, Narang et al, *Meth. Enzymol.*, 68:90, (1979); Itakura et al, *Ann. Rev. Biochem.*, 53:323–56 (1989); Brown et al, *Meth. Enzymol.*, 68:109, (1979); and U.S. Pat. No. 4,356,270, which description is incorporated herein by reference.

Derivation of a primer molecule from nucleic acids typically involves introducing a nucleic acid into an appropriate host as with a cloning vector, replication of the vector to increase the amount of cloned nucleic acid, followed by isolation of fragments or subfragments of the cloned nucleic acids. A description of techniques for subcloning nucleic acid fragments is found in Maniatis et al, *Molecular Cloning: A Laboratory Manual*, Cold Spring Harbor Laboratory, pp 390–401 (1982); and U.S. Pat. Nos. 4,416,988 and 4,403,036, which descriptions are incorporated herein by reference.

Template nucleic acid sequences to be hybridized in the present methods can be present in any nucleic acid-containing sample so long as the sample is in a form, with respect to purity and concentration, compatible with nucleic acid hybridization reaction. Isolation of nucleic acids to a degree suitable for hybridization is generally known and can be accomplished by a variety of means. See, for example, Maniatis et al, *Molecular Cloning: A Laboratory Manual*, Cold Spring Harbor Laboratory (1982); and Ausubel et al, *Current Protocols in Molecules Biology*, John Wiley and Sons (1987).

The hybridization reaction is carried out under predefined conditions that permit a primer to hybridize to its complementary nucleic acid template. "Hybridizing conditions," and grammatical equivalents thereof, as used herein, refer to the set of incubation time periods, temperature and pH parameters that permit the primer to anneal with the template sequence, typically to form a nucleic acid duplex. Such hybridization conditions depend on factors such as the length of the primer to be hybridized, the degree of complementarity between the primer and the template, the guanosine and cytidine content of the polynucleotide, the stringency of hybridization desired, and the presence of salts or additional reagents in the hybridization reaction admixture that may affect the kinetics of hybridization. Methods for optimizing hybridization conditions for a given hybridization reaction admixture are well known in the art but typically the hybridizing conditions involve solutions buffered to pH values between 4 and 9 at temperatures from 18° C. to 75° C., preferably about 37° C. through about 65° C., more preferably about 54° C., for time periods from 0.5 seconds to 24 hours, preferably about two minutes.

Hybridization can be carried out in a homogeneous or heterogeneous format as is well known. The homogeneous hybridization reaction occurs entirely in solution, in which both the primer and template sequences to be hybridized are present in soluble forms in solution. A heterogeneous reaction involves the use of a matrix that is insoluble in the reaction medium to which either the primer or template is bound. Also contemplated are the homogeneous hybridization reactions such as are conducted in the reverse transcription of isolated mRNA or viral RNA to form cDNA, dideoxy sequencing and other procedures using primer extension reactions in which primer hybridization is a first step.

Where the nucleic acid containing a template sequence is in a double-stranded (ds) form, it is preferably denatured as by heating or alkali treatment prior to conducting the hybridization reaction. The denaturation of the dsDNA can be carried out prior to admixture with a primer to be hybridized or can be carried out after admixture of the dsDNA with the primer. Where the primer itself is provided as a double-stranded molecule, it can also be denatured prior to admixture or it can be denatured concurrently with the template-containing dsDNA.

The primer extension reaction is performed using any suitable method. Preferably, a molar excess (for genomic nucleic acid, usually about $10^6$:1 primer:template) of the primer is admixed to the buffer containing the template strand. A large molar excess is preferred to improve the efficiency of the process. For polynucleotide primers of about 20 to 25 nucleotides in length, a typical ratio is in the range of 50 ng to 1 $\mu$g, preferably 250 ng, of primer per 100 ng to 500 ng of mammalian genomic DNA or per 10 to 50 ng of plasmid DNA.

Deoxyribonucleotide triphosphates (dNTPs) dATP, dCTP, dGTP, and dTTP are also admixed to the primer extension reaction admixture in amounts adequate to support the synthesis of primer extension products. The amounts used are readily determined by the skilled practitioner.

In a typical primer extension reaction, the hybridization admixture is heated through about 90°–100° C. for about one to 10 minutes, preferably from one to four minutes. After this heating period the solution is allowed to cool to room temperature to permit primer/template hybridization. To the cooled mixture is added an appropriate agent for inducing or catalyzing the primer extension reaction. The synthesis reaction can occur at from room temperature up to a temperature above which the inducing agent no longer functions efficiently. Thus, for example, if DNA polymerase is used as the inducing agent, a suitable temperature is generally no greater than about 40° C. unless the polymerase is heat-stable.

The inducing agent can be any compound or system that effects synthesis of primer extension products. Suitable enzymes for this purpose include, for example, *E. coli* DNA polymerase I, Klenow fragment of *E. coli* DNA polymerase I, T4 DNA polymerase, T7 DNA polymerase, recombinant modified T7 DNA polymerase, and other DNA polymerases, reverse transcriptases, and other enzymes that facilitate the primer extension reaction.

Heat-stable (thermophilic) DNA polymerases are particularly preferred in this regard as they are thermally stable in an automated temperature cycling PCR format. Representative heat-stable polymerases are the DNA polymerases isolated from *Bacillus stearothermophilus* (Bio-Rad, Richmond, Calif.), *Thermus thermophilus* (FINZYME, ATCC #27634), *Thermus species* (ATCC #31674), *Thermus aquaticus* strain TV 1151B (ATCC #25105), *Sulfolobus acidocaldarius*, described by Bukhrashuili et al, *Biochem. Biophys. Acta*, 1008: 102–7 (1989) and by Elie et al, *Biochem. Biophys. Acta*, 951:261–7 (1988), *Thermus filiformis* (ATCC #43280), the polymerase isolated from *Thermus flavus* (Molecular Biology Resources; Milwaukee, Wis.), and "Vent" polymerases (New England Biolabs, Beverly, Mass.). Particularly preferred are Taq DNA polymerase, available from a variety of sources including Perkin Elmer Cetus, (Norwalk, Conn.), Promega (Madison, Wis.) and Stratagene (La Jolla, Calif.), and AmpliTaq™ DNA polymerase, a recombinant Taq DNA polymerase available from Perkin-Elmer Cetus.

PCR is typically carried out by cycling the following steps on a reaction admixture: 1) heating to form denatured single-stranded templates and primers, 2) cooling to permit hybridization of primer to template, and 3) maintenance at predefined conditions to permit formation of primer extension products. Methods and systems for amplifying a specific nucleic acid sequence by PCR are described in U.S. Pat. Nos. 4,683,195 and 4,683,202, which are incorporated herein by reference, and in *PCR Technology*, Erlich, ed., Stockton Press (1989); Faloona et al, *Methods in Enzymol.*, 155:335–50 (1987); and *Polymerase Chain Reaction*, Erlich et al, eds., Cold Spring Harbor Laboratory Press (1989).

Detection of amplified nucleic acid product can employ any of a variety of well known techniques. In a preferred embodiment, the amplified product is separated on the basis of molecular weight by gel electrophoresis and the separated products are visualized with nucleic acid specific stains. Although numerous nucleic acid specific stains exist and would be suitable to visualize the electrophoretically separated nucleic acids, ethidium bromide is preferred.

Alternative methods for detecting the amplified nucleic acid product include hybridization-based detection means that use a labeled oligonucleotide probe capable of hybridizing to the amplified product. Exemplary of such detection means include the Southern blot analysis, ribonuclease protection analysis using in vitro labeled polyribonucleotide probes, and similar methods for detecting nucleic acids having specific nucleotide sequences. See, for example, Ausubel et al., *Current Protocols in Molecular Biology*, John Wiley & Sons, 1987.

In another approach for detecting the presence of a specific nucleic acid sequence, the deoxyribonucleotide triphosphates (dNTPs) used in the primer extension reaction include a label or indicating group that renders a primer extension product detectable. Typically such labels include radioactive atoms, chemically modified nucleotide bases, and the like. Suitable radioactive labels include $^3$H, $^{14}$C, $^{32}$P, and $^{35}$S, and the like.

Alternatives to radioactively labeled dNTPs are dNTPs modified chemically to contain metal complexing agents, biotin-containing groups, fluorescent compounds, and the like. A useful metal complexing agent is a lanthanide chelate compound formed by a fluorescent lanthanide metal and heta-diketonate ligands. The lanthanide hinds to the nucleic acid so that a fluorescent lanthanide/nucleic acid complex is formed. See U.S. Pat. Nos. 4,374,120, 4,569,790 and published International Patent Application Nos. EP0139675 and WO87/02708, which descriptions are incorporated herein by reference.

Biotin or acridine ester-labeled oligonucleotides and their use in polynucleotides have been described. See U.S. Pat. No. 4,707,404, published International Patent Application EP0212951 and European Patent No. 0087636. Useful fluorescent markers for oligonucleotides include fluorescein, rhodamine, Texas Red, NBD and the like.

Techniques for separating non-hybridized labeled probes from hybridized probes are well known, and typically involve the separation of single stranded from double stranded nucleic acids on the basis of their chemical properties. Frequently, a heterogeneous separation format is used in which non-hybridized probe is separated as by washing from the labeled DNA duplexes hound to an insoluble matrix. Exemplary of this technique are Southern blots in which the matrix is a nitrocellulose sheet and the label is $^{32}$P [Southern, *J. Mol. Biol.*, 98:503 (1975)].

D. Recombinant DNA Molecules

A recombinant DNA molecule comprising a vector operatively ligated to an above-described DNA segment is also contemplated. The recombinant DNA molecule (DNA construct) can facilitate amplification and/or expression of a subject DNA segment coding for a polypeptide of the invention.

A contemplated recombinant DNA molecule incorporates a cDNA segment coding for an amino acid residue sequence of a pan native apo B-100 epitope. Preferably, the apo B-100 cDNA is selected from those identified above in Table 1 with reference to the apo B-100 sequence depicted in FIG. 1 and in SEQ ID NO:2.

A particularly preferred recombinant DNA molecule, which is replicable upon transfection in a suitable host cell, contains a subject DNA segment encoding the amino acid residue sequence of apo B-100 shown in FIG. 1 from about residue 3430 through about residue 3510, corresponding to residue 217 through residue 297 of SEQ ID NO:1. A more preferred DNA construct encodes the apo B-100 amino acid residue sequence from about residue 3430 through about residue 3520, corresponding to residue 217 through residue 307 of SEQ ID NO:1. Preferably, the DNA construct contains a nucleotide sequence up through about 1130 base pairs encoding a subject polypeptide.

Typically, a recombinant DNA molecule of the present invention contains a DNA sequence coding for an immunologically "inert" linking peptide sequence fused to an above-described apo B-100 amino acid residue sequence. An exemplary sequence in this regard codes for a β-galactosidase moiety. Such a recombinant DNA molecule can be obtained by inserting a subject DNA segment into vector containing a gene encoding the β-galactosidase protein.

A contemplated recombinant DNA molecule (plasmid) can be circularized or linearized. An exemplary linearized molecule in this regard contains a before-described subject DNA segment encoding apo B-100. Similarly contemplated is a recombinant DNA molecule containing a nucleotide sequence coding for an amino acid residue sequence of apo A-I, which DNA molecule is operatively ligated in frame to the amino-terminus of a subject DNA segment encoding an apo B-100 sequence. Accordingly, a preferred linear recombinant DNA molecule comprises a nucleotide sequence encoding an amino acid residue sequence of apo A-I as shown in SEQ ID NO:3 from about amino acid residue 120 through about amino acid residue 135. More preferably, a plasmid encodes the amino acid residue sequence of apo A-I from about amino acid residue 19 through about amino acid residue 240. In the latter example, the nucleotide sequence encoding the apo A-I sequence contains about 663 nucleotides, or as the utilized double stranded molecule, 663 bp.

A further aspect of the invention relates to a recombinant DNA molecule that includes a DNA segment coding for an A-I/B-100 fusion polypeptide. The vector molecule permits amplification and/or expression of a fusion polypeptide that includes a before-described amino acid residue sequence of apo A-I operatively linked to a before-described, subject amino acid residue sequence of apo B-100.

Accordingly, an exemplary vector encoding a subject apo A-I/B-100 fusion polypeptide comprises:

(a) a first nucleotide sequence up through about 696 nucleotides in length that encodes an amino acid residue sequence including the amino acid residue sequence of the pan native apo A-I epitope shown in SEQ ID NO:3 from about amino acid residue 120 through about residue 135, with the second nucleotide sequence operatively ligated to the first nucleotide sequence; and (b) a second nucleotide sequence up through about 1130 nucleotides in length that encodes an amino acid residue sequence including the amino acid residue sequence of the pan native apo B-100 epitope shown in FIG. 1 from about amino acid residue 3430 through about amino acid residue 3510 corresponding to residues 217 through 297 of SEQ ID NO:1.

The choice of vector to which a DNA segment of the present invention is operatively ligated to form a subject recombinant DNA molecule depends on the functional properties desired, e.g., efficiency of transcription, efficiency of expression within the selected transformation host cell, location of restriction sites (as when PCR products are directly cloned into the vector), and the like. However, a vector of the present invention is at least capable of directing the replication of a DNA segment coding for a subject polypeptide.

Preferably, a chosen vector includes a prokaryotic replicon; i.e., a DNA sequence having the ability to direct autonomous replication and maintenance of the recombinant DNA molecule extrachromosomally in a prokaryotic host cell transformed therewith. Such replicons are well known in the art. In addition, a vector that includes a prokaryotic replicon preferably also includes a drug resistance gene so that hosts transformed with a vector can be readily screened. Typical bacterial drug resistance genes are those that confer resistance to ampicillin or tetracycline.

Vectors that include a prokaryotic replicon preferably include a prokaryotic promoter capable of directing the transcription of the instant polypeptide genes. A promoter is an expression control element formed by a DNA sequence that promotes binding of RNA polymerase and transcription of single-stranded DNA into messenger RNA (mRNA) molecules. Promoter sequences compatible with bacterial hosts, such as a tac promoter, are typically provided in plasmid vectors having convenient restriction sites for insertion of a DNA segment of the present invention. Typical of such vector plasmids are pUC8, pUC9, pBR322 and pBR329 available from Biorad Laboratories, (Richmond, Calif.) and pPL, pUR, and pKK223 available from Pharmacia (Piscataway, N.J.).

Expression vectors compatible with eukaryotic cells, preferably those compatible with vertebrate cells, can also be used to form a recombinant DNA molecule described before. Eukaryotic cell expression vectors are well known in the art and are available from several commercial sources. Typically, such vectors are provided with convenient restriction sites for insertion of the desired DNA segment. Typical of such vectors are pSVL and pKSV-10 (Pharmacia), pBPV-1pML2d (International Biotechnologies, Inc.), and pTDT1 (ATCC, #31255). A preferred drug resistance marker for use in vectors compatible with eukaryotic cells is the neomycin phosphotransferase (neo) gene. [Southern et al., *J. Mol. Appl. Genet.*, 1:327–341 (1982)].

Retroviral vectors that express a recombinant DNA of the present invention are also contemplated. The construction and use of retroviral vectors for expressing desired DNA molecules have been described. See, e.g., Sorge, et al., *Mol. Cell. Biol.*, 4:1730–37 (1984).

A number of methods are available to operatively link an instant DNA segment to a vector via complementary cohesive termini. For instance, complementary homopolymer tracts can be added to the DNA segment to be inserted and to the vector DNA. The vector and DNA segment are then hybridized by hydrogen bonding between the complementary homopolymer tails to form recombinant duplex DNA molecules. Alternatively, synthetic linkers containing one or more restriction sites can be used to join an instant DNA segment to a vector.

When a DNA segment is prepared by endonuclease restriction digestion, it can be treated with a DNA polymerase that removes protruding 3' single-stranded termini and fills in recessed 3' ends, thereby generating blunt-ended DNA segments. Blunt-ended DNA segments are incubated with a large molar excess of linker molecules in the presence of an enzyme, such as bacteriophage T4 DNA ligase, which is able to catalyze the ligation of blunt-ended DNA molecules. Thus, the products of the reaction are DNA segments covalently joined at their ends to linker sequences having restriction sites therein. The restriction sites of these DNA segments are then cleaved with the appropriate restriction enzyme and the segments ligated to an expression vector having termini compatible with those of the cleaved DNA segment. Synthetic linkers containing a variety of restriction endonuclease sites are commercially available from a number of sources including International Biotechnologies, Inc. (New Haven, Conn.).

Preferably, a subject DNA segment is ligated to a vector selected from the pUR class of vectors. See, Sambrook et al., *Molecular Cloning—A Laboratory Manual*, 2nd ed., Cold Spring Harbor Laboratory Press, (1989) pp 17.4–5. A particularly preferred vector for cloning a subject DNA segment, which encodes a truncated acid residue sequence of apo B-100, is pUR291.

A preferred and more preferred recombinant DNA molecule (expression vector) for transformation and expression in SURE ™ *E. coli* of a subject polypeptide, which immunologically mimics a pan native apo B-100 epitope, are designated plasmid "84" and plasmid "144" respectively SURE ™ *E. coli* separately transformed with plasmid "144" or plasmid "84" were deposited with the American Type Culture Collection (ATCC), 12301 Parklawn Drive, Rockville, Md. USA 20852. These deposits were made on Sep. 26, 1991 and received Accession No. 75112 and No. 75110, respectively.

A preferred expression vector for transformation and expression of an above-described fusion polypeptide, which immunologically mimics a pan native apo A-I epitope and a pan native apo B-100 epitope, is designated plasmid "137". SURE ™ *E. coli* transformed with plasmid "137" were deposited with the ATCC on Sep. 26, 1991, and received Accession No. 75111.

The before-discussed hybridoma and the above three bacterial deposits were made in compliance with the Budapest Treaty requirements that the duration of the deposits should be for 30 years from the date of deposit or for five years after the last request for the deposit at the depository or for the enforceable life of a U.S. patent that matures from this application, whichever is longer. A deposit will be replenished should it become non-viable at the depository.

E. Transformation and Purification

Also contemplated within the invention are cells stably transformed with a recombinant DNA molecule, including an expression vector, that contains an above-described DNA segment. The host cell can be either prokaryotic or eukaryotic. Preferred prokaryotic host cells are strains of *E. coli*, e.g., the *E. coli* strain SU- RE ™ commercially available from Stratagene Cloning Systems (La Jolla, Calif.). Preferred eukaryotic host cells include yeast and mammalian cells, preferably vertebrate cells such as those from mouse, rat, goat, or primate cell lines.

The above-noted SURE ™ strain of *E. coli* is particularly preferred as that strain remained stably transformed. *E. coli* strains DH5α (BRL), JM109 (Stratagene) and MC1601 (ATCC) could not be stably transformed. It is believed that the *E. coli* transformants prepared in Pease et al., *J. Biol. Chem.*, 265:553–568 (1990) were not stable transformants.

Transformation of a suitable host cell such as SURE ™ strain *E. coli* with a recombinant DNA molecule of the present invention is accomplished by well-known methods that typically depend on the type of vector used. With regard to transformation of prokaryotic host cells, see, e.g., Maniatis et al., *Molecular Cloning, A Laboratory Manual,* Cold Spring Harbor Laboratory, Cold Spring Harbor, N.Y. (1982). With regard to transformation of vertebrate cells with retroviral RNA vectors, see, e.g., Sorge et al., *Mol. Cell Biol.,* 4:1730–37 (1984).

Successfully transformed cells; i.e., those stably transfected with a recombinant DNA molecule of the present invention, can be identified by well-known techniques. For example, stably transformed cells can be cloned to produce monoclonal colonies. Cells from those colonies can be harvested, lysed and their DNA content examined for the presence of the desired DNA segment using a method such as that described by Southern, *J. Mol. Biol.*, 98:503 (1975).

In addition to directly assaying for the presence of the desired DNA segment, successful transformation can be confirmed by well-known immunological methods when the transformed cells express an above-described polypeptide. In this method, samples of cells suspected of being transformed are maintained under culture in an appropriate nutrient culture medium for a time period sufficient to express the polypeptide, harvested and assayed for a desired antigenicity using antibodies that immunoreact with (specifically bind to) a subject polypeptide. Preferred antibodies in this regard are produced by the hybridomas MB47 (ATCC HB 8746) when assaying for apo B-100 antigenicity and AI-11 (ATCC HB 9201) when assaying for apo A-I antigenicity.

Also contemplated are cultures of stably transformed host cells. Nutrient media useful for culturing transformed host cells are well known in the art and can be obtained from several commercial sources. When a mammalian host cell is employed a "serum-free" medium is preferably used.

Once stably transformed host cells are identified, those cells can be used in a method for expressing a subject polypeptide by maintaining (culturing) those transformed cells under appropriate culture conditions for a time period sufficient for the cells to express the polypeptide. The expressed polypeptide is preferably isolated (recovered) from the cultured cells.

Methods for recovering an expressed protein from a culture are well-known in the art. For instance, gel filtration, gel chromatography, ultrafiltration, electrophoresis, ion exchange, affinity chromatography and related techniques can be used to isolate an expressed protein from the culture. In addition, immunochemical methods, such as immunoaffinity, immunoadsorption, and the like, can be performed using well-known methods, as exemplified by the methods described herein.

F. Diagnostic Assays

A method for assaying the native apo B-100 level of a body fluid sample containing that protein is also contemplated within the invention. The targeted apoprotein (antigen) is detected in a body fluid sample such as a vascular fluid sample that contains apo B-100. Exemplary body fluid samples include plasma, serum or whole blood, but urine, semen, and cerebrospinal fluid can also be used. As native apo B-100 levels can be correlated to LDL cholesterol levels, the present invention affords a method for assaying the LDL cholesterol level in a body fluid sample.

Also contemplated is a method for assaying the amount of a second apolipoprotein, native apo A-I, in a body fluid sample. Since the amount of apo A-I in the sample can be correlated to the amount of HDL cholesterol in the sample, the invention affords a method for assaying the HDL cholesterol level of the sample.

Various well known heterogeneous and homogeneous protocols can be employed in competitive and direct binding assays for the presence, and preferably amount, of a targeted native apoprotein. Preferably, a solid-phase assay format is employed, which method permits physical separation of reaction product from potentially interfering reagents. Also preferred is a competitive binding protocol, which utilizes the competition of a subject polypeptide and native apoprotein in the assayed sample for binding to an antibody immunoreactive with both the subject polypeptide and native apoprotein.

Generally, an assay method of the present invention comprises admixing a body sample, e.g., human serum or plasma from a patient, in a liquid, aqueous medium such as water, normal saline, or a buffer, or plasma or other body fluid diluted therewith, with a subject polypeptide and an antibody composition containing pan anti-apo B-100 antibodies that immunoreact with the polypeptide and any native apo B-100 in the sample. The immunoreaction admixture thus formed is maintained under biological assay conditions for a time period sufficient for the antibody composition to immunoreact with antigens in the admixture; i.e., with both subject polypeptide and with native apo B-100. The presence, and preferably amount of any immunocomplex formed, as between native apo B-100 and pan anti-apo B-100 antibodies or, preferably, between a subject polypeptide and the pan anti-apo B-100 antibodies, is then determined. The amount of immunocomplex formed can then be related to the amount of native apo B-100 in the sample using well known techniques.

Along the lines described above for assaying native apo B-100 levels, a presently described method can also be utilized in an assay for a second apolipoprotein. Such a method comprises admixing a fluid body sample with a subject fusion apo A-I/B-100 polypeptide and an antibody composition containing pan anti-apo A-I antibodies. The pan anti-apo A-I antibodies immunoreact with native apo A-I in the sample and with the apo A-I/B-100 fusion polypeptide.

The immunoreaction admixture formed above is maintained under biological assay conditions for a time period sufficient for the anti-apo A-I antibodies to immunoreact with their antigens in the admixture. The amount of any immunocomplex formed, as between the fusion polypeptide and anti-apo A-I antibodies, is then determined. The amount of immunocomplex formed can then be related to the amount of native apo A-I in the sample, as discussed above.

The maintenance time for immunoreaction to take place can vary widely, as is well known. Maintenance times typically range from about one minute to about two hours, with times of about 30 to about 90 minutes being typically utilized.

The phrases "anti-apo B-100" and "anti-A-I antibodies" and "pan anti-apo B-100 antibodies" and "pan apo A-I antibodies" are utilized herein to mean antibody preparations that immunoreact with a before-described amino acid residue sequence of a pan native apo B-100 polypeptide epitope or of a pan native apo A-I epitope, and particularly a sequence containing the before-discussed amino acid residue sequence of the apo A-I molecule from amino acid residue position 120 to residue position 135. Particularly preferred antibody compositions are the before-discussed, deposited monoclonal antibodies such as MB47 and AI-11.

Polyclonal antibodies that immunoreact with a subject apo B-100 polypeptide or with a pan native apo A-I epitope are also contemplated. Such polyclonal antibodies can be prepared by immunization with LDL particles or apo B-100, or with HDL particles or apo A-I, respectively. A previously discussed dispersible apo B-100 polypeptide such as s5–s9 can also be used as an immunogen, as can a polypeptide containing the 120–135 amino acid residue sequence of apo A-I.

An antibody preparation can contain intact antibodies, or the binding site-containing (paratope-containing) portions thereof. Exemplary paratopecontaining portions include Fab, F(ab')$_2$ and F$_v$ portions as are well known. In addition, where an antibody Fc portion is present, that portion can have the amino acid residue sequence characteristic of an animal different from the paratope-containing portion. For example, a human Fc portion can be present along with a mouse binding site-containing portion as can be accomplished by genetic engineering techniques as are well known.

The "biological assay conditions" employed in the present assay methods are selected to maintain the biological activities of the sample being assayed, as well as the antibodies and polypeptides used in the assay. Typically acceptable "biological assay conditions" include a temperature in the range of about 4° C. through about 45° C., preferably about 37° C.; a pH value in the range of about 5 through about 9, preferably about 7; and an ionic strength ranging from that for distilled water to that of about 1M sodium chloride, preferably about that of physiological saline. Methods for optimizing such conditions are known to the skilled practitioner.

A predetermined amount of each of the various reagents is utilized in these assays. The predetermined amount of any reagent can vary with the assay. However, as the amount of apo B-100 and/or apo A-I is to be determined, the amounts of the standards such as a dispersible subject polypeptide or apo A-I/apo B-100 polypeptide must be known so that results can be quantified.

The manner of determining the presence or amount of an immunocomplex formed in a subject assay depends upon the method desired to identify the immunocomplex. For instance, an antibody used in the assay can be labeled prior to or subsequent to forming an immunocomplex with a dispersible antigenic polypeptide of the present invention or apolipoprotein. The labeled immunocomplex can be quantitated by methods appropriate for detecting the respective label, e.g., radiation detection when a radioactive label is used, fluorescence detection when a fluorescent is employed, reaction with avidin when a biotin label is employed, conversion of an enzyme substrate into a detectible product when an enzyme label is used, and the like. Alternatively, an unlabeled immunocomplex can be detected by forming an immunoreaction product between the immunocomplex and a labeled substance that specifically binds the immunocomplex, e.g., a labeled anti-antibody. A label is thereby attached to the assayed immunocomplex, which affords ready detection.

A particularly preferred method for assaying for the amount of native apo B-100 in a body fluid sample containing (or suspected of containing) that protein employs a dispersible subject polypeptide (antigen) affixed to the surface of a solid support to provide a "solid-phase" polypeptide. (Methods of affixation are discussed hereinafter.) Such a method, often referred to as a competitive assay, comprises the steps (a)–(c) below:

(a) admixing a predetermined amount of a body fluid sample containing native apo B-100 in a liquid medium with predetermined amounts of a dispersible subject polypeptide affixed to a solid support and pan anti-apo B-100 antibodies to form a solid-liquid phase admixture. The pan anti-apo B-100 antibodies immunoreact with the native apo B-100 of the sample and with the subject polypeptide. The polypeptide includes an amino acid residue sequence about 80 through about 375 residues of apo B-100 shown in FIG. 1 and includes the sequence from about residue 3430 through about residue 3510 corresponding to residues 217 through 297 of SEQ ID NO:1, and preferably the sequence from about residue 3430 through about 3520 corresponding to residues 217 through 307 of SEQ ID NO:1;

(b) maintaining the solid-liquid phase admixture under biological assay conditions for a time period sufficient for the pan anti-apo B-100 antibodies to immunoreact with the polypeptide and apo B-100 to form a solid-phase polypeptide/anti-apo B-100 immunocomplex and a liquid phase apo B-100/anti-apo B-100 immunocomplex, respectively;

(c) separating the solid and liquid phases; and (d) determining the amount of solid-phase polypeptide/anti-apo B-100 immunocomplex formed, and thereby the amount of native apo B-100 in the body fluid sample.

The above assay can be conducted by admixing the reagents in any order. A preferred order of admixture involves admixing the solid-phase polypeptide with the body fluid sample prior to admixing with the pan anti-apo B-100 antibodies.

Usually, a blocking agent, which blocks nonspecific binding of pan anti-apo B-100 antibodies with the solid phase matrix, is admixed with and any excess removed from the solid phase-affixed polypeptide prior to contacting the polypeptide with the anti-apo B-100 antibodies. A preferred blocking agent in this regard is BSA (bovine serum albumin), but any immunologically inert proteinaceous material can be used.

An especially preferred assay employs an enzyme-labeled MB47 antibody. A preferred method for determining the amount of solid-phase immunocomplex formed involves monitoring the reaction of enzyme-labeled MB47 antibody with a substrate for the enzyme, since the rate of such reaction depends on the amount of label affixed to the immunocomplex.

Another method for assaying the native apo B-100 level in a body fluid sample utilizes a subject polypeptide to inhibit the immunoreaction of native apo B-100 in the sample with pan anti-apo B-100 antibodies. The degree of inhibition observed can be correlated with the amount of native apo B-100 antigen in the sample by analogy to well known techniques. This method is often referred to as a competitive inhibition assay. The method comprises the steps (a)–(d) below:

(a) admixing a predetermined amount of a body fluid sample containing native apo B-100 in a liquid medium with predetermined amounts of a before-described subject polypeptide and solid phase-affixed pan anti-apo B-100 antibodies to form an admixture. The anti-apo B-100 antibodies immunoreact with the native apo B-100 of the sample and with the polypeptide;

(b) maintaining the admixture under biological assay conditions for a time period sufficient for the anti-apo B-100 antibodies to immunoreact with the polypeptide and apo B-100 to form a solid phase-affixed polypeptide/anti-apo B-100 immunocomplex and apo B-100/anti-apo B-100 immunocomplex;

(c) separating the solid and liquid phases; and (d) determining the amount of solid phase-affixed polypeptide/anti-apo B-100 immunocomplex formed, and thereby the amount of native apo B-100 in the body fluid sample.

A subject polypeptide is here conjugated to a label or indicating means such as one selected from the group of a radioactive element, enzyme, biotin, fluorescent, and chemiluminescent labels. The amount of indicating mean or label bound can then be used to determine the amount of apo B-100 in the sample.

A subject polypeptide can also be employed in standardizing an assay for the amount of native apo B-100 in a body fluid sample. In this procedure, a known amount of a subject polypeptide can be quantitated with an indicating means, such as a labeled antibody, and a body fluid sample containing an unknown amount of apo B-100 can be quantitated with the same indicating means. When these assay results are correlated, the unknown amount of native apo B-100 is determined. This standardization process can be used with any apo B-100 assay described herein.

The standardization method comprises the following steps:

(a) admixing in a liquid medium first predetermined amounts of a body fluid sample containing native apo B-100 and pan anti-apo B-100 antibodies to form a first admixture, in which the anti-apo B-100 antibodies immunoreact with the native apo B-100 of the sample;

(b) maintaining the first admixture under biological assay conditions for a time period sufficient for the anti-apo B-100 antibodies to immunoreact with the native apo B-100 in the sample to form a native apo B-100/anti-apo B-100 immunocomplex;

(c) admixing second predetermined amounts of the same pan anti-apo B-100 antibodies and a subject polypeptide in a liquid medium to form a second admixture in which the anti-apo B-100 antibodies immunoreact with the polypeptide;

(d) maintaining the second admixture under biological assay conditions for a time period sufficient for the anti-apo B-100 antibodies to immunoreact with the polypeptide to form a polypeptide/anti-apo B-100 immunocomplex; and (e) determining the amounts of native apo B-100/anti-apo B-100 and polypeptide/anti-apo B-100 immunocomplexes formed, and thereby the amount of native apo B-100 in the body fluid sample.

Preferably, the anti-apo B-100 antibodies of the above method are conjugated to a label selected from the group consisting of radioactive, enzyme, biotin, fluorescent, and chemiluminescent labels. It is also preferred that the anti-apo B-100 antibodies, be affixed to a solid support.

In another aspect of a standardization assay, the determination step (e) comprises:

(i) admixing the native apo B-100/anti-apo B-100 immunocomplex in a liquid medium with second antibodies immunoreactive with the native apo B-100 to form a third admixture, in which the second antibodies are operatively linked to a first label;

(ii) maintaining the third admixture under biological assay conditions for a period of time sufficient for the second antibodies to immunoreact with the native apo B-100/anti-apo B-100 immunocomplex to form a second antibody/native apo B-100/anti-apo B-sandwich complex;

(iii) determining the amount of first label affixed to the second antibody/native apo B-100/anti-apo B-100 sandwich complex, thereby determining the relative amount of native apo B-100/anti-apo B-100 immunocomplex formed;

(iv) admixing the polypeptide/anti-apo B-100 immunocomplex in a liquid medium with third antibodies immunoreactive with the polypeptide or the bound antibodies to form a fourth admixture, the third antibodies operatively linked to a second label;

(v) maintaining the fourth admixture under biological assay conditions for a period of time sufficient for the third antibodies to immunoreact with the polypeptide/anti-apo B-100 immunocomplex to form a third antibody/polypeptide/anti-apo B-100 sandwich complex; and (vi) determining the amount of second label affixed to the third antibody/polypeptide/anti-apo B-100 sandwich complex, thereby determining the amount of polypeptide/anti-apo B-100 immunocomplex formed and the true amount of native apo B-100 in the sample.

Preferably, the second antibody above is an MB24 antibody secreted by the hybridoma having ATCC Accession No. HB 8742 and the third antibody is an anti-beta-galactosidase antibody where a beta-galactosidase fusion protein is used as the subject polypeptide. Antibodies that immunoreact with another epitope of a subject polypeptide, as can be formed using that polypeptide as an immunogen, and whose immunoreaction is not inhibited by the bound anti-apo B-100 antibodies can also be used as the third antibodies. Label-linked anti-MB47 antibodies such as enzyme- or radio-labeled goat anti-mouse antibodies can also be used. It is also preferred that the first and second markers are identical.

A before-described dispersible apo B-100 subject polypeptide including a fusion polypeptide is thus used as the long-awaited standard for the otherwise unstable intact, whole apo B-100 molecule.

In addition to a method for assaying native apo B-100 in a body fluid sample, a method for assaying the levels of native apo A-I in the sample is contemplated. In particular, a preferred method of assaying for the amounts of native apo B-100 and apo A-I antigens in a body fluid sample employs a subject apo A-I/B-100 fusion polypeptide (a recombinant apo A-I/B-100 antigen) affixed to the surface of a solid support. The method comprises the following steps:

(a) admixing a predetermined amount of the body fluid sample to be assayed in a liquid medium with predetermined amounts of a dispersible subject fusion polypeptide affixed to a solid support, pan anti-apo B-100 antibodies, and pan anti-apo A-I antibodies enumerated previously to form a solid-liquid admixture. The anti-apo B-100 antibodies immunoreact with the native apo B-100 of the sample and with the polypeptide, and the anti-apo A-I antibodies immunoreact with the native apo A-I of the sample and with the fusion polypeptide;

(b) maintaining the solid-liquid admixture under biological assay conditions for a time period sufficient for the anti-apo B-100 antibodies and anti-apo A-I antibodies to immunoreact with the respective antigens of the fusion polypeptide to form solid-phase fusion polypeptide/anti-apo B-100 and fusion polypeptide/anti-apo A-I immunocomplexes; and (c) determining the amounts of solid-phase fusion polypeptide/anti-apo B-100 and fusion polypeptide/anti-apo A-I immunocomplexes formed, and thereby the amounts of native apo B-100 and native apo A-I in the sample.

Again, the order of admixture of the above reagents is not critical; however, the reagents are preferably admixed substantially simultaneously. The above assay can be carried out using a single solid support for both assays where the antibodies to each antigen are differently labeled. Exemplary different labels or markers are radioisotopes such as $^3$H and $^{131}$I that emit beta, and beta and gamma radiation, respectively, of different energies. These labels are used with a gated radiation counter. Another exemplary system uses horseradish peroxidase conjugated to one antibody and alkaline phosphatase linked to the other, along with their usual substrates. Here, optical densities at two different wavelengths are determined to obtain the desired data.

Another assay of the invention employs pan anti-apo B-100 antibodies immobilized on a first support and pan anti-apo A-I antibodies immobilized on a second support. When two apoproteins are assayed, the antibodies can be provided on two different supports. Alternatively, the antibodies can be affixed to the same support, in which case different detection means must be associated with each kind of antibody, or the different antibodies can be localized to different regions, e.g., cells or rows, in a grid or otherwise partitioned pattern on the surface of a solid matrix.

Also contemplated is a "contrived control" method for assaying the amount of native apo B-100 in a lipoprotein-containing body fluid sample. This method is termed "contrived control" because it employs a subject polypeptide as a reference or control in delipidated plasma in an assay for native apo B-100 so that both the assayed sample and control contain similar plasma proteins and salts and have similar viscosities.

In this assay, the delipidated body fluid sample comprises a portion of the liquid medium in which the subject polypeptide and anti-apo B-100 antibodies are admixed. Preferably, the amount of delipidated body fluid is the same as the amount of body fluid sample that is assayed. A contrived control assay can be used with any assay discussed herein that utilizes a separate subject polypeptide-containing aqueous composition, such as standardized, assay.

G. Diagnostic Systems

A diagnostic system, typically in kit form, is also contemplated that can be employed in carrying out the above-described assay methods. A diagnostic system of the invention comprises a container (package) that includes at least a subject polypeptide. The polypeptide is provided in an amount sufficient to perform at least one assay and is usually provided as a separately packaged reagent.

The polypeptide can be labeled, as when conjugated to a marker; however, the polypeptide can also be unlabeled. The polypeptide can be provided neat, dissolved or suspended in a suitable liquid vehicle such as a buffer, lyophilized, bound to a solid support, or in another convenient physical form, as is readily apparent.

Another preferred kit comprises an above-described apo A-I/B-100 fusion polypeptide, pan anti-apo B-100 antibodies, and pan anti-apo A-I antibodies as discussed previously. Exemplary pan anti-apo B-100 antibodies include MB47 antibodies and exemplary pan anti-apo A-I antibodies include AI-11 antibodies.

Preferably, an indicating (marking or labeling) means is also provided that permits indication of an immunocomplex formed upon reaction of a subject polypeptide with an antibody immunoreactive with the polypeptide. In some formats, as is apparent from the before-described methods, a labelling means is preferably conjugated to a subject polypeptide. In other formats, a labelling means is preferably associated, as by conjugation, with an antibody immunoreactive with the polypeptide. Thus, a preferred kit contains a labeled antibody, such as a labeled murine antibody, that immunoreacts with another epitope of a subject polypeptide also provided in the kit. Optionally, a labeled antibody is provided that immunoreacts with the immunocomplex formed upon reaction of a subject polypeptide with an antibody immunoreactive with the polypeptide. An example of a latter-described labeling means is a labeled goat anti-mouse antibody that is useful for immunoreacting with before-described murine monoclonal antibodies such as MB47 and AI-11.

When a label is associated with a reagent provided in a kit of the invention, it can be selected from any of those commonly available. Exemplary labels include $^{111}$In, $^{99}$Tc, $^{67}$Ga, $^{125}$I, $^{131}$I, non-radioactive labels, such as biotin and enzyme-linked antibodies, chromophoric labels such as fluorescein, phycoerythrin, rhodamine, chemiluminescent labels, and the like. Preferred enzyme labels include horseradish peroxidase (HRPO), alkaline phosphatase, and leuciferin. Preferred chromophoric labels include fluorescein and the Immune-lite chemiluminescent visualization system distributed by Bio-Rad (Richmond, Calif.).

Methods for linking a label to an immunoglobulin or protein are well-known. For instance, antibody molecules produced by a hybridoma can be labeled by metabolic incorporation of radioisotope-containing amino acids provided as a component in the culture medium [Galfre et al., *Meth. Enzymol.*, 73:3–46 (1981)]. The techniques of protein conjugation or coupling through activated functional groups are particularly applicable. See, for example, Aurameas, et al., *Scand. J. Immunol.*, Vol. 8, Suppl. 7:7–23 (1978), Rodwell et al., *Biotech.*, 3:889–894 (1984), and U.S. Pat. Nos. 4,493,795 and 3,996,345, which disclosures are incorporated herein by reference.

A diagnostic system of the invention can also include a specific binding agent. A "specific binding agent" is a chemical species capable of selectively binding a reagent species of a diagnostic system described herein, but is not itself an antibody molecule. Exemplary specific binding agents are complement proteins or fragments thereof, protein A, and the like that react with an antibody molecule when the antibody is part of an immunocomplex described above.

In preferred embodiments, a specific binding agent is labeled; however, it can be unlabeled. When the specific binding agent is not labeled, the specific binding agent is typically used as an amplifying means or reagent. In these embodiments, a specific-binding indicating means, such as a labeled antibody, is also provided that specifically binds to the amplifying means when the amplifying means is bound to an immunocomplex described herein and provides a signal for the presence of the immunocomplex.

A diagnostic kit of the invention can be used conveniently in an "ELISA" format to detect the presence or quantity of a native apolipoprotein in a body fluid sample, such as serum, plasma or urine, using a before-described method. An "ELISA" format is an enzyme-linked immunosorbent assay that employs an antibody or antigen bound to a solid phase and an enzyme-antigen or enzyme-antibody conjugate to detect and quantify the amount of antibody or antigen present in a sample. A description of the ELISA technique is found in Chapter 22 of the 4th Edition of *Basic and Clinical Immunology* by D. P. Sites et al., published by Lange Medical Publications of Los Altos, Calif. in 1982. Various ELISA formats are also described in U.S. Pat. Nos. 3,654,090; 3,850,752; 3,817837; 3,875,011; and 4,016,043, which disclosures are incorporated herein by reference.

More preferably, an antibody or antigen reagent, including a recombinant antigen (fusion polypeptide), is affixed to a solid matrix to form a solid support, which is separately packaged in a subject diagnostic system. Also, a plurality of solid supports such as the wells of a 96-well plastic microtiter plate can be employed, as when a plurality of antibodies are employed in an above-described assay method or when a plurality of assays are to be carried out.

An antibody or antigen reagent of a diagnostic system or as used in a before-described assay method is typically affixed to a solid matrix by adsorption from an aqueous medium, although other modes of affixation well known to those skilled in the art can be used, such as covalent binding, binding by an antibody that itself is bound to the matrix, or binding of an antibody to a solid support via adsorbed protein A. Solid matrix materials useful in this regard include the derivatized cross-linked dextran available under the trademark SEPHADEX from Pharmacia Fine Chemicals (Piscataway, N.J.), agarose in its derivatized and/or cross-linked form, polystyrene beads about 1 micron through about 5 millimeters in diameter available from Abbott Laboratories of North Chicago, Ill., polyvinyl chloride, polystyrene, cross-linked polyacrylamide, nitrocellulose- or nylon-based webs such as sheets, strips or paddles, tubes, plates, the wells of a microtiter plate such as those made from polystyrene or polyvinylchloride, and the like. Microtiter wells in the form of strips and plates are particularly preferred.

A reagent provided in a diagnostic system described herein can be provided in solution, as a liquid dispersion or as a substantially dry powder, e.g., in lyophilized form. Where an indicating means is an enzyme, the enzyme's substrate can also be provided in a separate package of the diagnostic system. Usually, the reagents are packaged under an inert atmosphere. A solid support, such as a microtiter plate, and one or more buffers can also be included as separately packaged elements in this diagnostic assay system.

A more preferred diagnostic system, in one package, is useful for detection of native apo B-100 and native apo A-I. An exemplary kit in this regard includes the following in separate containers:

(a) a dispersible subject apo A-I/B-100 fusion polypeptide affixed to a microtiter plate;
(b) HRPO-labeled MB47 antibodies in lyophilized form; and
(c) non-HRPO-labeled, e.g., alkaline phosphatase labeled, AI-11 antibodies in lyophilized form.

Another exemplary kit includes the following in separate containers:

(a) a dispersible subject apo A-I/B-100 fusion polypeptide in lyophilized form;
(b) HRPO-labeled MB47 antibodies; and
(c) non-HRPO-labeled AI-11 antibodies.

Preferably, a kit, such as described above, contains a blocking agent, such as bovine serum albumin (BSA), for blocking nonspecific binding of antibodies to polypeptide. Also, a kit containing an HRPO-labeled reagent preferably includes: (i) a supply of hydrogen peroxide of known concentration; (ii) a visualizing oxidative dye precursor such as OPD (o-phenylenediamine); and (iii) a solution of a quenching agent such as 4N sulfuric acid.

A kit also is preferably provided with instructions for use of the packaged reagent. The instructions typically include a tangible expression describing the reagent concentration or at least one assay parameter such as the relative amounts of reagent and sample to be admixed, maintenance time periods for reagent/sample admixtures, temperature, buffer conditions, and the like.

In a further aspect of the invention, a diagnostic system contains means for recording and/or correlating data obtained in the above-described assays. Thus, in one embodiment, data are recorded with a tangible medium, e.g., computer storage, chart paper, and the like. The data can be automatically input and stored using analog/digital (A/D) instrumentation, which is commercially available. Also, the data can be recalled and reported or displayed as desired for best presenting the instant correlations of data. Accordingly, materials for correlating data, such as instrumentation and software suitable for use with the present methods, can be provided in a presently-described diagnostic system and are contemplated as within the scope of the present invention.

A diagnostic system of the invention can be contained in a conventional package, including glass and plastic (e.g., polyethylene, polypropylene and polycarbonate) bottles, vials, plastic and plastic-foil laminated envelopes, paper, and the like.

EXAMPLES

The following examples do not limit the scope of the invention but are presented merely to illustrate certain aspects of the present invention.

Example 1: Mapping of MB47 epitope of apo B-100

The MB47 epitope of apo B-100 was mapped using β-gal fusion proteins containing the polypeptide of interest. This was effected by cloning PCR-amplified apo B-100 cDNA into a polycloning site located at the 3' terminus of the lacZ gene of the plasmid pUR291 [Ruther et al., *EMBO J.*, 2:1791 (1983)]. The pUR291 vector has a unique PstI site within the polycloning site. See, Sambrook et al., *Molecular Cloning—A Laboratory Manual*, 2nd ed., Cold Spring Harbor Laboratory Press, pp. 17.4–5, (1989) for a restriction map of the relevant cloning site.

Exemplary polypeptide regions of apo B-100 that were mapped by this method are identified in Table 1 hereinbefore; the primers used to generate the amplified cDNAs are identified in Tables 3 and 4.

Notably, one primer set found ineffective for preparing an immunoreactive polypeptide were the oligonucleotides denoted #37 (forward) and #35 (reverse) which had the following nucleotide sequences:

5'-ATGCGGATCCAAATTAGAGGGCACCACAAGA-3'
(#37, Forward) which is identified as SEQ ID NO: 17.

5'-GTGCCCTGCAGTTATCACTTCACTGAAGACCGTGTGCT-3'
(#35, Reverse) which is identified as SEQ ID NO: 18.

These primers coded for sequence positions 3349 through 3506, nucleotide positions 10,059 through 10,770. This primer set encoded a polypeptide (3349–3506) substantially identical to positions 3351–3506 reported in [Pease et al., *J. Biol. Chem.*, 265:553 (1990)] as apparently useful in Western blots, but exhibited no binding in assays conducted herein.

A. Cloning of 483 bp Apo B-100 cDNA

The procedure for cloning the PCR-amplified apo B-100 cDNA into a pUR291 vector is described hereinbelow for the 483 bp apo B-100 coding fragment identified in Table 2; however, the same general procedure was used for other domains.

Briefly, vector pUR278 (a vector similar to pUR291) containing a 1.4 kb apo B-100 cDNA was obtained from R. Pease of the Medical Research Council Clinical Research Centre, Harrow HA1 3UJ, United Kingdom [Pease et al., supra]. The apo B-100 cDNA of this vector starts at nucleotide 9639 and terminates with nucleotide 11,709 [Ludwig et al. *DNA*, 6:363 (1987); Knott et al., *Nucl. Acids Res.*, 14:7501 (1986)]. This vector was used as a template for generating the apo B-100 inserts.

The pUR291 plasmid was selected to express the targeted apo B-100 fragments as β-gal fusion proteins. The pUR291 plasmid carries an entire active β-gal gene including promoter, and generally works well for preparing fusion proteins containing an N-terminal β-galactosidase. The 3' terminus of the β-gal gene has convenient BamHI, PstI and HindIII restriction sites. Also, pUR291 confers ampicillin resistance to the transformed host.

The 483 base pair (bp) apo B-100 nucleotide sequence extending from base 10,287 to base 10,770 was amplified using the 1.4 kb insert of pUR278 as a template. Thus, forward and reverse primers #46 and #130, respectively of Table 3, were hybridized with pUR278 and the resulting hybrid was subjected to standard PCR conditions (Perkin Elmer Cetus; Norwich, Conn.). After 40 PCR cycles, the amplification reaction was halted and the product containing the amplified 483 bp nucleotide sequence was separated from the reaction mixture.

As the #46 and #130 primers (Table 3) carried BamHI and PstI restriction sites, the amplified product could be cut with those enzymes and cloned directly into the pUR291 vector, previously cut with BamHI and PstI. Although the 483 bp-containing sequence actually contained more than that number of base pairs because of the bases added to create the BamHI and PstI restriction sites, the produced fragment and the fragment resulting from cleavage with those enzymes is referred to for convenience as a 483 bp fragment or 483 bp PCT product.

B. Cloning of Apo B-100 Sequences

The isolated 483 bp-containing PCR product was digested with BamHI and PstI restriction enzymes (10 μl each) for one hour and 37° C. to generate cohesive termini. The 483 bp sticky ended fragment was isolated and ligated into the BamHI- and PstI-linearized plasmid pUR291 using T4 DNA ligase (Bethesda Research Laboratory; Grand Island, N.Y.).

The other recombinant apo B-100 polypeptides noted in Table 1 and Table 2, and the primers used for their preparation as noted in Tables 3 and 4, were similarly prepared, and utilized as discussed below.

C. Transformation in SURE™ *E. coli*.

The resulting plasmid vector was isolated and used to transform SURE™ *E. coli* following the supplier's protocol (Stratagene Cloning Systems; La Jolla, Calif.). Briefly, 100 μl of the cells were aliquotted into a pre-chilled 15 ml Falcon 2059 polypropylene tube and 1.7 ||1 of fresh 1:10 2-mercaptoethanol were added to the cells to give a 25 mM final concentration. The reaction mixture in the tube was swirled gently and chilled in ice for 10 minutes. Approximately 0.1–50 ng plasmid were added to the cells and the mixture swirled gently. A control insert of 1 μl of pBR322 was admixed with another 100 μl of cells and swirled gently.

The tubes were placed in ice for 30 minutes then heat pulsed in a 42° C. water bath for 45 seconds. The tubes were returned to ice for two minutes. About 0.9 ml of preheated (42° C.) SOC medium [20 g Bactotryptone, 5 g yeast extract, 0.5 g NaCl, autoclaved, then prior to use, 2 ml of 20 percent glucose and 1 ml of MgCl$_2$/MgSO$_4$ (12 g MgSO$_4$/9.5 g MgCl$_2$/100 ml water) per 100 ml of solution were added and filter sterilized] were added, and the mixture was incubated for one hour at 37° C. with shaking at 225 rpm.

D. Screening of *E. coli* Colonies

Transformed cells carrying the correct insertion were identified by plating transformation mixture on appropriate antibiotic plates. Thus, 15 amp-resistant colonies (plated on media containing 50 μg/ml of ampicillin) were picked. The inserted DNA was isolated using the minilysate method [Ish-Horowicz et al., *Nucl. Acids Res.*, 9:2989 (1981)] and a portion of the DNA was cut with BamHI and PstI to generate a 483 bp fragment. The DNA samples were analyzed on 1 percent ethidium bromide-stained agarose gels to confirm the correct clones with the 483 bp DNA band. One of the plasmids so formed, designated plasmid "127", was induced with IPTG (isopropylthiogalactosidase) to give the targeted β-gal fusion polypeptide which was subsequently reacted with MB47 in mapping studies.

E. MB47 Binding Studies

The binding properties of monoclonal antibody MB47 with the expressed apo B-100 polypeptide fragments were then determined. Briefly, SURE ™ E. coli cells expressing the fusion polypeptide encoded by the "127" plasmid or other plasmids were harvested. Cell extracts were clarified and their protein concentration was determined by a modified Lowry assay [Markwell et al., Anal. Biochem., 87:206 (1978)].

Proteinaceous bands were separated by electrophoresis of the extracts on polyacrylamide gradient (3–20 percent) gels containing 1 percent SDS (sodium dodecylsulfate). The bands in the gel were blotted onto Immune-Lite blotting membrane (BioRad; Richmond, Calif.) using a semi-dry blotter. The presence of the desired expression product in the isolated bands was confirmed with monoclonal antibodies AI-11 and MB47 or for β-galactosidase activity using the Immune-Lite chemiluminescent kit (BioRad).

Fusion polypeptide-containing inclusion bodies were prepared according to the protocol of Pease et al., J. Biol. Chem., 265:553–568 (1990). Briefly, competent E. coli cells were transformed with the "127" plasmid or other plasmids encoding a fusion polypeptide of interest as described above. The transformed cells were grown in a rich nutrient broth (TYE broth) supplemented with 50 μg/ml ampicillin, and production of the fusion polypeptide was induced with IPTG. E. coli cells containing the fusion polypeptide were collected by centrifugation and the cells were lysed by the addition of lysozyme to a concentration of 0.2 mg/ml.

The lysed cells were then treated with bovine pancreatic deoxyribonuclease and sodium deoxycholate. This admixture was subjected to high speed centrifugation to pellet the fusion protein-containing inclusion bodies. This pellet was resuspended in a solution of 50 mM Tris·HCl, 75 mM NaCl and 1 mM EDTA (Solution A, pH 7.5) containing sodium deoxycholate. This admixture was again centrifuged at high speed, after which the pellet was resuspended in Solution A plus 2-mercaptoethanol (70 mM final concentration) and Triton-X100 (1 percent final concentration). After a 30 minute incubation, this admixture was subjected to high speed centrifugation.

In a departure from the method of Pease et al., the fusion polypeptides were purified from the inclusion bodies by the following protocol. Contaminating proteins were precipitated by the addition of 20 percent saturated ammonium sulfate to the supernatant fraction. These proteins were removed by high speed centrifugation, and the supernatant fraction from this step was also treated with 20 percent saturated ammonium sulfate. After another high speed centrifugation step, the supernatant fraction containing the fusion polypeptides was collected and dialyzed overnight in phosphate-buffered saline. After dialysis, the solution was clarified by brief high speed centrifugation. This procedure provided a dispersible fusion polypeptide substantially free of a denaturing surfactant in that the Triton X-100 was substantially removed during purification, and SDS was never used.

A Dynatech Immulon 2 microtiter plate was coated with the purified fusion polypeptide obtained above. The fusion polypeptide samples were diluted to a concentration of about 45 μg using 10 mM sodium carbonate-bicarbonate buffer solution (pH 9.6). Wells in the microtiter plate were coated with 100 μl of the diluted fusion polypeptide solution. The plate was incubated for about 18 hours at 4° C. covered with an acetate plate cover, after which the plate was washed once with a standard PBS (phosphate buffered saline)-Tween wash solution (0.05 percent Tween 20, 0.05M phosphate buffer, pH=7.6). Nonspecific binding sites of the proteins were blocked with 200 μl of 3 percent BSA (bovine serum albumin) in PBS and the admixture was incubated at 37° C. for one hour.

A labeled MB47 solution was prepared using MB47 conjugated to HRPO (horseradish peroxidase) as described by P. K. Nakane, Immunofluorescence and Related Techniques, W. Knapp ed., (1978) Elsevier, Holland, pp.215. The HRPO-conjugated MB47 was diluted with the 3 percent BSA in PBS solution to give a 0.1 percent conjugate solution.

Approximately 100 μl of the conjugate solution was added to the fusion polypeptide-containing wells, covered with an acetate plate cover, and incubated at room temperature on an orbital shaker for one hour. The plate was then washed five times with the standard PBS/Tween solution.

Approximately 100 μl of an o-phenylenediamine (OPD; Sigma; St. Louis, Mo.) substrate solution was added to each well and the admixture was incubated at room temperature for 30 minutes. The reaction was quenched with 50 μl of 4N $H_2SO_4$ per well and the plate was read at 490 nm. Notably, the measurements of optical density at 490 nm, relative to a control polypeptide, were high enough to indicate MB47 reactivity without a need for or hinderance of protein solubilization by SDS.

The results of these studies indicated that the affinities of MB47 for the examined fusion polypeptides can be classified into at least three groups. In the first group of polypeptides, MB47 immunoreacted strongly with the polypeptide fragments encoded by the about 483, 408, 345, and 282 base pair sequences corresponding to polypeptides s5–s8 of Table 2. In fact, the immunoaffinity of MB47 for these apo B-100 fragments is comparable to that for the about 1128 bp, 377 residue apo B-100 fragment (s9 in Table 1).

The above studies also revealed that the 471, 372, 276 and 243 bp cDNA noted in Table 2 code for apo B-100 polypeptide fragments s1–s4 also immunoreacted strongly with MB47. However, the affinity of this second group of fusion polypeptides for MB47 is notably less than that for the first group of proteins. Finally, a third group of fusion polypeptides, encoded by the 171, 111, 90 and 45 bp nucleotide sequences noted in Table 2, showed little affinity for MB47.

Example 2: Preparation of apo A-I/B-100 Dual Constructs

Apo A-I/B-100 fusion proteins were prepared as further fusions with a β-galactosidase fragment. The syntheses are exemplified by the procedure used to form plasmid "137", which is described below.

A. Amplification of Apo A-I cDNA

A 663 bp nucleotide sequence of apo A-I cDNA was PCR-amplified from plasmids containing the cDNA. Briefly, human apo A-I cDNA containing a 696 bp sequence including the desired sequence was obtained from Dr. Jan Breslow of the Rockefeller University (New York, N.Y.). The cDNA contained PstI restriction sites at either end of the sequence. The cDNA was cloned into the pBR322 vector (Pharmacia; Piscataway, N.J.) and subjected to PstI restriction under standard conditions. Vector pBR322 has a PstI restriction site within the amp gene.

After ligation and transformation, the resulting transformed hosts were screened for ampicillin-sensitivity and tetracycline resistance. A plasmid derived from one such ampicillin-sensitive, tetracycline-resistant transformed host was designated plasmid pa101.

Approximately 5 μg of pa101 was digested with 50 units of Pst I restriction enzyme and the linearized DNA was precipitated with ethanol. Approximately 100 ng of collected DNA was used as a PCR template (Perkin Elmer) to amplify a 663 bp apo A-1 cDNA that did not contain the signal sequence (residues 1-18). The forward primer, designated oligonucleotide #90, was prepared by Research Genetics (Huntsville, Ala.) and had the following nucleotide sequence:

(SEQ ID NO: 19)
5'-ATGTCTGCAGCGGCATTTCTGGCAGCAA-3'
      PstI

The reverse primer, designated oligonucleotide #72, was prepared by Genetic Design (Houston, Tex.) and had the following nucleotide sequence:

5'-GTGCCCTGCAGTTATCATTGGCGGAGGTCCTCGAGCGC-3' (SEQ ID NO: 20)
      PstI

B. Cloning and Identification of Apo A-I

The PCR generated apo A-I product was digested with 20 units of PstI restriction enzyme and ligated into the PstI site of the plasmid pUR291 (Pharmacia). The resultant plasmids were screened for proper insertion. SURE ™ E. coli (Stratagene Cloning Systems; La Jolla, Calif.) was transformed with the plasmid and 100 amp-resistant colonies (plated on media containing 50 μg/ml of ampicillin) were picked on a grid and screened by hybridization with oligonucleotide primer #90 radioactively labeled with $^{32}P$. Ten positive colonies were selected and checked for correct orientation by digestion with BamHI and XhoI restriction enzymes. Plasmids with the proper orientation generated the predicted 1200 bp fragment. One of the plasmids, designated plasmid "85", was used in formation of the apo A-I/B-100 dual construct of plasmid "137" as described below.

C. Formation of apo A-I/B-100 Dual Construct

Synthesis of apo A-I/B-100 dual construct plasmid "137" from apo A-I plasmid "85" was performed as described below. Briefly, plasmid "85" was linearized by digestion with HindIII at a unique site within the polylinker of original plasmid pUR291. The cohesive termini on the linearized DNA were converted to blunt-ends by digestion with T4 polymerase according to the manufacturer's instructions.

The linearized plasmid was cleaved at the unique XhoI site present at the 3' terminus of the apo A-I gene. The resultant linearized fragment of plasmid "85" had a cohesive XhoI site at the 3' terminus of the apo A-I gene and a blunt end at the 5' end of the plasmid.

A 483 bp apo B-100 insert was generated by PCR. In particular, plasmid "1.5 Kb" (Pease et al., supra), which contained a 1.5 kb apo B-100 insert in pUR291 was used as a template in a PCR protocol to amplify the 483 bp fragment domain. This region was previously identified (in plasmid "127") as containing all of the information necessary for optimal MB47 binding. The 483 bp region was amplified using forward and reverse primers #132 and #130 (as shown in Table 3). A 483 bp PCR product having an XhoI site upstream of the 5' sequence terminus and a PstI site downstream of the 3' sequence terminus was thereby prepared, which also contained a 5 bp "buffer" sequence at the 3' terminus. Digestion of the PCR-amplified DNA with XhoI thereby generated a cohesive XhoI 5' terminus and a blunt 3' end.

The PCR-generated apo B-100 DNA fragment from plasmid "1.5 Kb" obtained above was ligated directly into the before-discussed linearized plasmid "85" having a blunt 5' end and a XhoI site at the 3' end using the protocol outlined by the vendor (Pharmacia). Plasmids containing the apo A-I/B-100 insert were screened for the correct placement and orientation by restriction endonuclease double digests using BamHI/XhoI and XhoI/PstI. A correct clone, designated plasmid "137", was identified and used in subsequent transformations of SURE ™ E. coli. Expressed fusion polypeptides were analyzed on Western blots to confirm the presence of the dual epitope following a procedure like that described above for apo B-100 polypeptides.

Example 3: Assay of Plasma with Apo A-I/B-100 Standard

An assay of human plasma for its LDL and HDL content can be performed using an above-described apo A-I/B-100 fusion protein as a reference standard. The feasibility of such a reference standard was demonstrated by the following study.

A. Isolation of Dual Construct and Control Proteins

Cells containing the "137" or pUR291 (control) plasmids were fermented at 37° C. for 9 hours (including induction) to obtain a cell paste. The cell pastes were resuspended in sonication buffer (10 mg/g cells). The sonication buffer was prepared from Buffer A (0.1M Tris-HCl, pH=7.8; 1 mM $MgCl_2$; 0.5 mM $Na_2EDTA$; 0.1M NaCl) containing 0.1M L-arginine hydrochloride, 10 mg/l PMSF (phenyl methyl sulfonyl fluoride), and 70 mM 2-ME (2-mercaptoethanol) freshly added. Lysozyme was added to a final concentration of 0.5 mg/ml and the mixture was maintained for 20 minutes. Cells were disrupted by sonication (Artek; Farmingdale, N.Y.) at 80 watts for five minutes on ice.

The raw extract was centrifuged at 10000 x g for 10 minutes, the supernatant discarded, and the pellet was resuspended in the same volume of Buffer A containing 70 mM 2-ME. The cell paste obtained was treated as previously described. After sonication and subsequent centrifugation, the supernatant was discarded and the pellet was resuspended in PBS containing 5 percent SDS buffer (and 70 mM 2-ME) at 2.5 ml/g cells to give a stock solution of the protein.

B. Immunoaffinity Studies on Dual Construct Versus Control Proteins

A Dynatech-Immulon 2 microtiter plate was coated with varying dilutions of the above stock apo A-I/B-100 fusion protein and control proteins. A stock solution containing 0.95 μg/100 μl of the rehydrated apo A-I/B-100 fusion protein expressed by plasmid "137" was diluted at ½, ¼, ⅛, 1/16, 1/32, and 1/64 dilutions using a 10 mM sodium carbonate-bicarbonate buffer (pH 9.0). A pUR291 stock solution (prepared at 395.0 μg/100 μl) was similarly diluted. The microtiter wells were each coated with approximately 100 μl of solution—two wells for each protein at each dilution. Each fusion polypeptide was assayed with MB47 and AI-11 antibodies.

The coated microtiter plate was covered with an acetate plate and incubated about 18 hours (overnight) at 4° C. The plate was washed with the above standard PBS-Tween wash buffer and was blocked with 200 μl of a PBS+3 percent BSA solution and was incubated at 37° C. for one hour.

A 1:1000 dilution of HRPO-labeled MB47 antibodies was prepared using the PBS+3 percent BSA diluent. A 1:1000 dilution of HRPO-labeled AI-11 was prepared using the PBS+3 percent BSA diluent.

Approximately 100 μl of MB47 conjugate were added to two sets of wells and approximately 100 μl of the AI-11 conjugate were added to the other two sets of wells. The wells were covered with an acetate plate and incubated at room temperature on an orbital shaker for one hour. The plate was washed five times with PBS/Tween. Approximately 100 μl of an OPD substrate were added to each well and the solutions were incubated for 30 minutes at room temperature. The reactions were then quenched with 4N $H_2SO_4$ and read at 490 nm. The results are presented in Table 5 below.

TABLE 5

ELISA of Dual Construct ("137") Fusion Protein and Control (pUR291) Binding to MB47 and AI-11

| Dilution[2] | MB47[1] | | AI-11[1] | |
|---|---|---|---|---|
| | "137" | pUR291 | "137" | pUR291 |
| ½ | 1.3 | 0.10 | 1.0 | 0.10 |
| ¼ | 0.46 | 0.12 | 0.60 | 0.08 |
| ⅛ | 0.14 | 0.10 | 0.20 | 0.08 |
| 1/16 | 0.10 | 0.04 | 0.14 | 0.07 |
| 1/32 | 0.10 | 0.02 | 0.14 | 0.05 |
| 1/64 | 0.08 | 0.01 | 0.12 | 0.04 |

[1]Optical density at 490 nm.
[2]Dilution of stock solutions

The results of the studies described above indicated preferential binding between the assayed antibodies and the dispersible apo A-I/B-100 fusion polypeptide. Significantly, the results demonstrate that the fusion polypeptide does not need to be solubilized, e.g., in a denaturing concentration of SDS (sodium dodecyl sulfate), for use.

C. Studies in Urea-Free Buffers

A cell preparation as discussed in (A), above, was again used as the source of the fusion polypeptide. Here, however, the buffer system used contained PBS and 5 percent SDS to solubilize the E.coli lysate following sonication.

After three sonications and resuspension into the buffer after a 30 minute, 16,000Xg centrifugation, the fusion stock solution prepared from the supernatant was loaded onto a model 491 Bio-Rad preparative SDS-polyacrylamide gel electrophoresis system. Two ml fractions were collected and dialyzed with 25 mM ammonium bicarbonate to remove substantially all of the SDS.

Fifty μl aliquots from every fifth dialyzed fraction were coated on the walls of 96-well polystyrene microtiter plates, incubated for one hour at room temperature and washed as discussed in (B), above, and then nonspecific binding sites were blocked with BSA in PBS as noted in (B), above. Fifty μl of purified monoclonal antibodies AI-11 and MB47 at 2.17 mg/ml and 2.44 mg/ml in 3 percent BSA in PBS were separately admixed with the coated wells and maintained at 4° C. for about 18 hours (overnight). After washing the plates to remove unreacted antibody, radiolabeled ($^{125}I$) goat anti-mouse IgG (at $2.2 \times 10^5$ cpm/μl) (50 μl in 97.2 percent TCA) was added to each well and maintained at 4° C. for four hours. After washing, the bound radioactivity was counted.

The results of this study indicated that proteins with AI-11 and MB47 co-eluted from the preparative gel. Although a minimal amount of SDS was likely present in the fusion polypeptide preparation, that amount did not inhibit use of the fusion polypeptide as an antigen for these studies, and that fusion polypeptide was substantially free of the denaturing surfactant.

Twenty-five fusion polypeptide-containing fractions (50 ml) were pooled and studied in another, similar study that also included HDL and LDL as coatings on the walls of the plates. The results of this study showed that there was sufficient fusion polypeptide in the pool, without further concentration, to perform HDL and LDL assays with monoclonals AI-11 and MB47, respectively. Those results also again showed that the minimal amount of SDS present in the fusion polypeptide preparation did not interfere with the antigenicity of the A-I/B-100 fusion polypeptide as is usually the case. Although an ammonium bicarbonate buffer was used for these studies, other buffers normally used for coating microtiter plates can also be used.

Although the present invention has been described in some detail by way of illustration and example for purposes of clarity and understanding, certain obvious modifications can be practiced within the scope of the appended claims.

What is claimed is:

1. A nonnatural polypeptide having an amino acid residue sequence of apo B-100 up through 375 residues in length that includes the amino acid residue sequence of apo B-100 shown in SEQ ID NO:1 from residue 217 through residue 297, which polypeptide immunoreacts with antibodies secreted by the hybridoma MB47 having ATCC Accession No. HB 8746, said polypeptide being dispersible in an aqueous medium in the substantial absence of a denaturing surfactant.

2. The polypeptide of claim 1 that includes the amino acid residue sequence of apo B-100 from residue 216 through residue 310.

3. The polypeptide of claim 2 that includes the amino acid residue sequence of apo B-100 from residue 216 through residue 331.

4. The polypeptide of claim 3 that includes the amino acid residue sequence of apo B-100 from residue 216 through residue 352.

5. The polypeptide of claim 4 that includes the amino acid residue sequence of apo B-100 from residue 216 through residue 377.

6. The polypeptide of claim 5 that includes the amino acid residue sequence of apo B-100 from residue 1 through residue 377.

7. The polypeptide of claim 1 that includes an amino acid residue sequence of apo B-100 that is selected from the group consisting of residues 205 to 297, 173 through 297, 140 through 297 and 216 through 310.

8. The polypeptide of claim 1 further having a beta-galactosidase moiety operatively linked to the amino-terminus thereof.

9. The polypeptide of claim 1, wherein said polypeptide includes the amino acid residue sequence of apo B-100 from residue position 216 through position 377 operatively linked to the C-terminus beta-galactosidase.

10. A fusion polypeptide that contains:

(a) a first amino acid residue sequence of apo A-I up through 250 residues in length that includes the amino acid residue sequence of apo A-I shown in SEQ ID NO:3 from residue 120 through residue 135, said fusion polypeptide immunoreacting with anti-apo A-I antibodies secreted by a hybridoma selected from the group consisting of:

AI-4 (ATCC HB 8744),
AI-7 (ATCC HB 8745),
AI-9 (ATCC HB 8741),
AI-10 (ATCC HB 9200),
AI-11 (ATCC HB 9201),
AI-12 (ATCC HB 9202),
AI-13 (ATCC HB 9203),
AI-14 (ATCC HB 9204), and
AI-18 (ATCC HB 9570); and (b) a second amino acid residue sequence of apo B-100 up through 375 residues in length that includes the amino acid residue sequence of apo B-100 shown in SEQ ID NO:1 from residue 217 through residue 297, said fusion polypeptide immunoreacting with antibodies secreted by the hybridoma MB47 (ATCC HB 8746);

said second amino acid residue sequence operatively linked to the carboxy-terminus of said first amino acid residue sequence.

11. The fusion polypeptide of claim 10, wherein the first and second amino acid residue sequences are linked by a third amino acid residue sequence up through residues in length.

12. The fusion polypeptide of claim 11, wherein the first amino acid residue sequence includes the amino acid residue sequence of apo A-I shown in SEQ ID NO:3 from residue 19 through residue 240.

* * * * *